US010221215B2

United States Patent
Arora et al.

(10) Patent No.: US 10,221,215 B2
(45) Date of Patent: *Mar. 5, 2019

(54) HYDROGEN BOND SURROGATE MACROCYCLES AS MODULATORS OF RAS

(71) Applicant: New York University, New York, NY (US)

(72) Inventors: Paramjit S. Arora, Cold Spring Harbor, NY (US); Dafna Bar-Sagi, New York, NY (US); Anupam Patgiri, New York, NY (US); Kamlesh Yadav, New York, NY (US)

(73) Assignee: New York University, New York, NY (US)

(*) Notice: Subject to any disclaimer, the term of this patent is extended or adjusted under 35 U.S.C. 154(b) by 2 days.

This patent is subject to a terminal disclaimer.

(21) Appl. No.: 14/641,297

(22) Filed: Mar. 6, 2015

(65) Prior Publication Data

US 2015/0239935 A1 Aug. 27, 2015

Related U.S. Application Data

(63) Continuation of application No. 14/003,219, filed as application No. PCT/US2012/027617 on Mar. 2, 2012, now Pat. No. 8,987,412.

(60) Provisional application No. 61/449,472, filed on Mar. 4, 2011.

(51) Int. Cl.
| | |
|---|---|
| *C07K 7/08* | (2006.01) |
| *C07K 14/47* | (2006.01) |
| *C07K 7/06* | (2006.01) |
| *A61K 38/08* | (2006.01) |
| *A61K 38/10* | (2006.01) |
| *A61K 38/00* | (2006.01) |

(52) U.S. Cl.
CPC .............. *C07K 7/08* (2013.01); *A61K 38/08* (2013.01); *A61K 38/10* (2013.01); *C07K 7/06* (2013.01); *C07K 14/4705* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,202,332 B2 | 4/2007 | Arora et al. | |
| 8,034,959 B2* | 10/2011 | Ng et al. | ................. 548/433 |
| 8,987,412 B2* | 3/2015 | Arora | ................. C07K 7/08 |
| | | | 530/300 |

FOREIGN PATENT DOCUMENTS

| | | |
|---|---|---|
| WO | 00/05258 A1 | 2/2000 |
| WO | 2010/033879 A2 | 3/2010 |

OTHER PUBLICATIONS

Patgiri et al, Solid-phase synthesis of short a-helices stabilized by the hydrogen bond surrogate approach (Nature Protocols, 5, 2010, 1857-1865).*
Patgiri et al, A Hydrogen Bond Surrogate Approach for Stabilization of Short Peptide Sequences in a-Helical Conformation (Accounts of Chemical Research 1289-1300 Oct. 2008 vol. 41, No. 10).*
Bao et al, Dynamical Binding of Hydrogen-Bond Surrogate Derived Bak Helices to Antiapoptotic Protein Bcl-xL (J. Phys. Chem. B 2009, 113, 3565-3571).*
International Preliminary Report on Patentability and Written Opinion for PCT/US2012/027617 (dated Sep. 19, 2013).
Consonni et al., "Structure Determination and Dynamics of Peptides Overlapping the Catalytic Hairpin of the Ras-Specific GEF Cdc25Mm," Biochemistry 42:12154-62 (2003).
Garbay et al., "Inhibitors of RAS Signal Transduction as Antitumor Agents," Biochem. Pharmacol. 60:1165-69 (2000).
Patgiri et al., "An Orthosteric Inhibitor of the Ras-Sos Interaction," Nat. Chem. Biol. 7(9):585-87 (2012).
Patgiri et al., "Solid Phase Synthesis of Hydrogen Bond Surrogate Derived α-Helices: Resolving the Case of a Difficult Amide Coupling," Org. Biomol. Chem. 8:1773-76 (2010).
PCT/US2012/027617, International Search Report (dated Jun. 15, 2012).
Monera et al., "Relationship of Sidechain Hydrophobicity and α-Helical Propensity on the Stability of the Single-stranded Amphipathic α-Helix," Journal of Peptide Science 1:319-329 (1995).
Boriack-Sjodin et al., "The Structural Basis of the Activation of Ras by Sos," Nature 394:337-43 (1998).

* cited by examiner

*Primary Examiner* — Sergio Coffa
(74) *Attorney, Agent, or Firm* — LeClairRyan PLLC

(57) ABSTRACT

The present invention relates to peptides having one or more stable, internally-constrained HBS α-helices, where the peptide is capable of interacting with Ras and related proteins.

59 Claims, 17 Drawing Sheets

Specification includes a Sequence Listing.

SEQUENCE LISTING

```
<160> NUMBER OF SEQ ID NOS: 19

<210> SEQ ID NO 1
<211> LENGTH: 16
<212> TYPE: PRT
<213> ORGANISM: Artificial
<220> FEATURE:
<223> OTHER INFORMATION: Peptide mimic of amino acids 929-944 of the
      alpha-H sequence of Sos
<220> FEATURE:
<221> NAME/KEY: MISC_FEATURE
<222> LOCATION: (2)..(2)
<223> OTHER INFORMATION: Xaa can be any amino acid residue
<220> FEATURE:
<221> NAME/KEY: MISC_FEATURE
<222> LOCATION: (4)..(5)
<223> OTHER INFORMATION: Xaa can be any hydrophobic amino acid residue
<220> FEATURE:
<221> NAME/KEY: MISC_FEATURE
<222> LOCATION: (6)..(6)
<223> OTHER INFORMATION: Xaa can be any amino acid residue
<220> FEATURE:
<221> NAME/KEY: MISC_FEATURE
<222> LOCATION: (7)..(7)
<223> OTHER INFORMATION: Xaa can be any hydrophobic amino acid residue
<220> FEATURE:
<221> NAME/KEY: MISC_FEATURE
<222> LOCATION: (8)..(8)
<223> OTHER INFORMATION: Xaa can be any amino acid residue
<220> FEATURE:
<221> NAME/KEY: MISC_FEATURE
<222> LOCATION: (9)..(9)
<223> OTHER INFORMATION: Xaa can be any hydrophobic amino acid residue
<220> FEATURE:
<221> NAME/KEY: MISC_FEATURE
<222> LOCATION: (11)..(11)
<223> OTHER INFORMATION: Xaa can be any amino acid residue
<220> FEATURE:
<221> NAME/KEY: MISC_FEATURE
<222> LOCATION: (12)..(12)
<223> OTHER INFORMATION: Xaa can be any hydrophobic amino acid residue
<220> FEATURE:
<221> NAME/KEY: MISC_FEATURE
<222> LOCATION: (14)..(15)
<223> OTHER INFORMATION: Xaa can be any amino acid residue

<400> SEQUENCE: 1

Phe Xaa Gly Xaa Xaa Xaa Xaa Xaa Xaa Leu Xaa Xaa Glu Xaa Xaa Asn
1               5                   10                  15

<210> SEQ ID NO 2
<211> LENGTH: 16
<212> TYPE: PRT
<213> ORGANISM: Artificial
```

```
<220> FEATURE:
<223> OTHER INFORMATION: Residues 929-944 of the alpha-H sequence of Sos

<400> SEQUENCE: 2

Phe Phe Gly Ile Tyr Leu Thr Asn Ile Leu Lys Thr Glu Glu Gly Asn
1               5                   10                  15

<210> SEQ ID NO 3
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 3

Phe Glu Gly Ile Tyr Arg Thr Asp Ile Leu Arg Thr Glu Glu Gly Asn
1               5                   10                  15

<210> SEQ ID NO 4
<211> LENGTH: 17
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 4

Phe Gly Glu Gly Ile Tyr Arg Thr Asp Ile Leu Arg Thr Glu Glu Gly
1               5                   10                  15

Asn

<210> SEQ ID NO 5
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 5

Ala Glu Gly Ile Tyr Arg Thr Asp Ile Leu Arg Thr Glu Glu Gly Asn
1               5                   10                  15

<210> SEQ ID NO 6
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 6

Ala Glu Gly Ile Tyr Arg Ala Asp Ile Leu Arg Thr Glu Glu Gly Asn
1               5                   10                  15

<210> SEQ ID NO 7
<211> LENGTH: 11
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 7

Phe Glu Gly Ile Tyr Arg Thr Asp Ile Leu Arg
1               5                   10
```

```
<210> SEQ ID NO 8
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 8

Phe Glu Gly Ile Tyr Arg Thr Glu Leu Leu Lys Ala Glu Glu Ala Asn
1               5                   10                  15

<210> SEQ ID NO 9
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 9

Phe Glu Gly Ile Tyr Arg Leu Glu Leu Leu Lys Ala Glu Glu Ala Asn
1               5                   10                  15

<210> SEQ ID NO 10
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 10

Ala Glu Gly Ile Tyr Arg Leu Glu Leu Leu Lys Ala Glu Ala Ala Ala
1               5                   10                  15

<210> SEQ ID NO 11
<211> LENGTH: 11
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 11

Phe Glu Gly Ile Tyr Arg Leu Glu Leu Leu Lys
1               5                   10

<210> SEQ ID NO 12
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos
<220> FEATURE:
<221> NAME/KEY: MISC_FEATURE
<222> LOCATION: (12)..(12)
<223> OTHER INFORMATION: Xaa is 2-aminoisobutyric acid

<400> SEQUENCE: 12

Phe Glu Gly Leu Leu Arg Leu Trp Leu Arg Lys Xaa Glu Glu Ala Asn
1               5                   10                  15

<210> SEQ ID NO 13
<211> LENGTH: 16
<212> TYPE: PRT
```

```
<213> ORGANISM: Artificial
<220> FEATURE:
<223> OTHER INFORMATION: Peptide mimic of residues 929-944 of the
      alpha-H sequence of Sos
<220> FEATURE:
<221> NAME/KEY: MISC_FEATURE
<222> LOCATION: (12)..(12)
<223> OTHER INFORMATION: Xaa is 2-aminoisobutyric acid
<220> FEATURE:
<221> NAME/KEY: MISC_FEATURE
<222> LOCATION: (15)..(15)
<223> OTHER INFORMATION: Xaa is 2-aminoisobutyric acid

<400> SEQUENCE: 13

Phe Glu Gly Leu Leu Arg Leu Trp Leu Arg Lys Xaa Glu Glu Xaa Asn
1               5                   10                  15

<210> SEQ ID NO 14
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos
<220> FEATURE:
<221> NAME/KEY: MISC_FEATURE
<222> LOCATION: (12)..(12)
<223> OTHER INFORMATION: Xaa is 2-aminoisobutyric acid
<220> FEATURE:
<221> NAME/KEY: MISC_FEATURE
<222> LOCATION: (15)..(15)
<223> OTHER INFORMATION: Xaa is 2-aminoisobutyric acid

<400> SEQUENCE: 14

Phe Glu Gly Ile Tyr Arg Leu Glu Leu Leu Lys Xaa Glu Glu Xaa Asn
1               5                   10                  15

<210> SEQ ID NO 15
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 15

Phe Glu Gly Leu Leu Arg Leu Trp Leu Arg Lys Ala Glu Glu Ala Asn
1               5                   10                  15

<210> SEQ ID NO 16
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 16

Phe Glu Ala Ile Tyr Arg Leu Glu Leu Leu Lys Ala Glu Glu Ala Asn
1               5                   10                  15

<210> SEQ ID NO 17
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 17
```

```
Phe Glu Ala Ile Tyr Arg Leu Glu Lys Leu Lys Ala Glu Glu Ala Asn
1               5                   10                  15

<210> SEQ ID NO 18
<211> LENGTH: 16
<212> TYPE: PRT
<213> ORGANISM: Artificial
<220> FEATURE:
<223> OTHER INFORMATION: Peptide mimic of residues 929-944 of the
      alpha-H sequence of Sos
<220> FEATURE:
<221> NAME/KEY: MISC_FEATURE
<222> LOCATION: (10)..(10)
<223> OTHER INFORMATION: There is a lactam bridge between residues 9
      and 13

<400> SEQUENCE: 18

Phe Glu Ala Ile Tyr Arg Leu Glu Lys Leu Lys Ala Glu Glu Ala Asn
1               5                   10                  15

<210> SEQ ID NO 19
<211> LENGTH: 18
<212> TYPE: PRT
<213> ORGANISM: Artificial
<220> FEATURE:
<223> OTHER INFORMATION: Peptide mimic of residues 929-944 of the
      alpha-H sequence of Sos

<400> SEQUENCE: 19

Phe Glu Gly Ile Tyr Arg Leu Glu Lys Leu Lys Ala Glu Glu Ala Asn
1               5                   10                  15

Arg Arg
```

HYDROGEN BOND SURROGATE MACROCYCLES AS MODULATORS OF RAS

CROSS-REFERENCE TO RELATED APPLICATIONS

This application is a continuation of U.S. patent application Ser. No. 14/003,219, filed Mar. 2, 2012, which is a national stage application under 35 U.S.C. § 371 of PCT Application No. PCT/US2012/027617, filed Mar. 2, 2012, which claims the benefit of U.S. Provisional Patent Application Ser. No. 61/449,472, entitled "Hydrogen Bond Surrogate Macrocycles as Modulators of Ras," filed on Mar. 4, 2011, each of which is incorporated herein by reference in its entirety.

STATEMENT AS TO FEDERALLY SPONSORED RESEARCH

This invention was made with government support under grant numbers R01GM073943 and R01GM078266, both awarded by the National Institutes of Health. The government has certain rights in the invention.

BACKGROUND OF THE INVENTION

Aberrant receptor tyrosine kinase (RTK) signaling is a major underlying cause of various developmental disorders and hyperproliferative diseases (Blume-Jensen et al., "Oncogenic kinase signalling". *Nature* 2001, 411, 355). A primary transduction mechanism by which RTK signals are propagated to intracellular pathways involves the ligand-dependent activation of the small guanine nucleotide binding protein Ras (FIG. 1) (Buday et al., "Many faces of Ras activation." *Biochim. Biophys. Acta* 2008, 1786, 178). Accordingly, design of Ras signaling pathway inhibitors has been an active area of research for anticancer therapy (Downward et al., "Targeting Ras signalling pathways in cancer therapy." *Nat. Rev. Cancer* 2003, 3, 11). The rate-limiting step in Ras activation process is the conversion of Ras-GDP to Ras-GTP through an exchange reaction that is catalyzed by the Ras specific guanine nucleotide exchange factor Sos (FIG. 2). The highly conserved catalytic domain (Rem+cdc25) of Sos interacts with Ras at a helical hairpin composed of the α-H and α-I helices (FIG. 3). The helical hairpin may be capable of nucleotide dissociation from Ras and subsequent down-regulation of the Ras pathway (Sacco et al., "The isolated catalytic hairpin of the Ras-specific guanine nucleotide exchange factor Cdc25(Mm) retains nucleotide dissociation activity but has impaired nucleotide exchange activity." *Febs Lett.* 2005, 579, 6851). The high resolution structures of this complex suggest that the α-H helix is the only portion of the helical hairpin that makes direct contact with Ras, while the α-I helix may only serve to stabilize the α-H conformation (Boriack-Sjodin, et al. "The structural basis of the activation of Ras by Sos." *Nature* 1998, 394, 337).

Inhibitors of the Ras-Sos interactions would be valuable as tools to dissect this complex signaling pathway and as leads for anticancer drug design. However, despite the availability of a high resolution crystal structure of the Ras/Sos complex since 1998, direct inhibitors of this complex have not been reported. Therefore, there remains a need for methods and compositions for treating developmental disorders and hyperproliferative diseases by inhibiting undesirable activities associated with Ras proteins, for example by inhibition of the Ras/Sos complex. The invention addresses these and other needs.

SUMMARY OF THE INVENTION

In one aspect, the invention provides a peptide having a stable, internally-constrained alpha-helix, wherein said alpha helix is constrained by a crosslink formed by a carbon-carbon bond-forming reaction, and further wherein the peptide mimics at least a portion of a protein capable of interacting with a Ras protein. In some embodiments, the protein capable of interacting with a Ras protein is Sos. For example, the peptide mimics at least a portion of an αA, αB, αC, αD, αE, αF, αG, αH, αI, αJ, or αK helix of Sos. In some instances, the peptide mimics at least a portion of the α-H helix of Sos. In one embodiment, the peptide mimics amino acids 929-944 of the α-H sequence of Sos. For example, the peptide comprises a sequence of the formula FXGZZXZXZLXZEXXN (SEQ ID NO: 1) where X is any amino acid residue and Z is a hydrophobic residue. In other embodiments, the peptide comprises an amino acid sequence of Table 1, and has an internally-constrained alpha-helix spanning residues 1 through 4 of the amino acid sequence.

In some embodiments, the peptide comprises the formula:

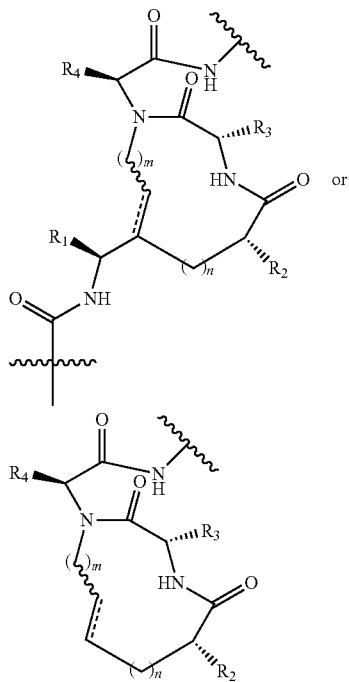

where
- - - - - is a single or double carbon-carbon bond;
∿∿∿ is a single bond and is cis or trans when - - - - - is a double bond;
n is 1 or 2;
m is zero or any positive integer;
$R_1$, $R_2$, $R_3$ and $R_4$ are independently hydrogen, an amino acid side chain, an alkyl group, or an aryl group.

For example, m is 1 or 2. In other embodiments, n is 1 or 2.

The invention also provides a pharmaceutical composition comprising a peptide according to the invention and a pharmaceutically acceptable vehicle.

In another aspect, the invention provides a method of inhibiting Ras signaling in a cell, comprising contacting the cell with an effective amount of a composition comprising a peptide having a stable, internally-constrained alpha-helix, wherein said alpha helix is constrained by a crosslink formed by a carbon-carbon bond-forming reaction, and further wherein the peptide mimics at least a portion of a protein capable of interacting with a Ras protein. In some embodiments, the protein capable of interacting with a Ras protein is Sos. For example, the peptide mimics at least a portion of an αA, αB, αC, αD, αE, αF, αG, αH, αI, αJ, or αK helix of Sos. In some instances, the peptide mimics at least a portion of the α-H helix of Sos. In one embodiment, the peptide mimics amino acids 929-944 of the α-H sequence of Sos. For example, the peptide comprises a sequence of the formula FXGZZXZXZLXZEXXN (SEQ ID NO: 1) where X is any amino acid residue and Z is a hydrophobic residue. In other embodiments, the peptide comprises an amino acid sequence of Table 1, and has an internally-constrained alpha-helix spanning residues 1 through 4 of the amino acid sequence.

In some embodiments, the peptide comprises the formula:

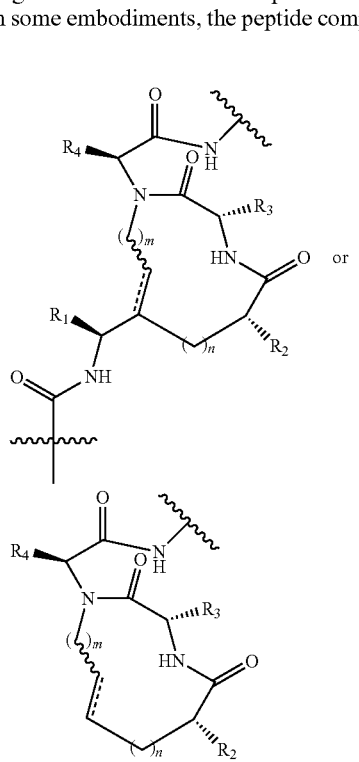

where
----- is a single or double carbon-carbon bond;
∿∿∿∿ is a single bond and is cis or trans when ----- is a double bond;
n is 1 or 2;
m is zero or any positive integer;
$R_1$, $R_2$, $R_3$ and $R_4$ are independently hydrogen, an amino acid side chain, an alkyl group, or an aryl group.

For example, m is 1 or 2. In other embodiments, n is 1 or 2.

The invention further provides a method of treating cancer in a subject in need thereof, comprising administering to the subject a peptide having a stable, internally-constrained alpha-helix, wherein said alpha helix is constrained by a crosslink formed by a carbon-carbon bond-forming reaction, and further wherein the peptide mimics at least a portion of a protein capable of interacting with a Ras protein. For example, the peptide comprises a sequence of the formula FXGZZXZXZLXZEXXN (SEQ ID NO: 1) where X is any amino acid residue and Z is a hydrophobic residue. In other embodiments, the peptide comprises an amino acid sequence of Table 1, and has an internally-constrained alpha-helix spanning residues 1 through 4 of the amino acid sequence. In some embodiments, the peptide comprises the formula:

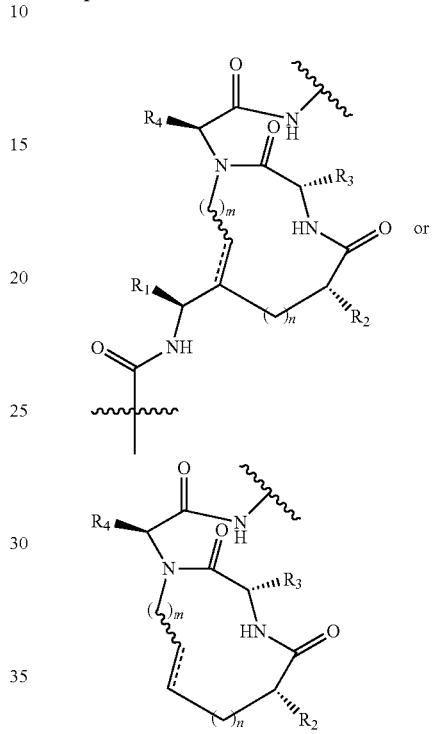

where
----- is a single or double carbon-carbon bond;
∿∿∿∿ is a single bond and is cis or trans when ----- is a double bond;
n is 1 or 2;
m is zero or any positive integer;
$R_1$, $R_2$, $R_3$ and $R_4$ are independently hydrogen, an amino acid side chain, an alkyl group, or an aryl group.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8a shows attenuation of EGF-induced Ras activation by HBS 7. FIG. 8b shows downregulation of Ras activation by direct interference with the Ras/Sos complex. FIG. 8c shows suppression of EGF-induced ERK activation by HBS 7. FIG. 8d shows a reduction in the intensity and duration of EGF-induced ERK activation following treatment with HBS 7.

DETAILED DESCRIPTION OF THE INVENTION

Figure 1:
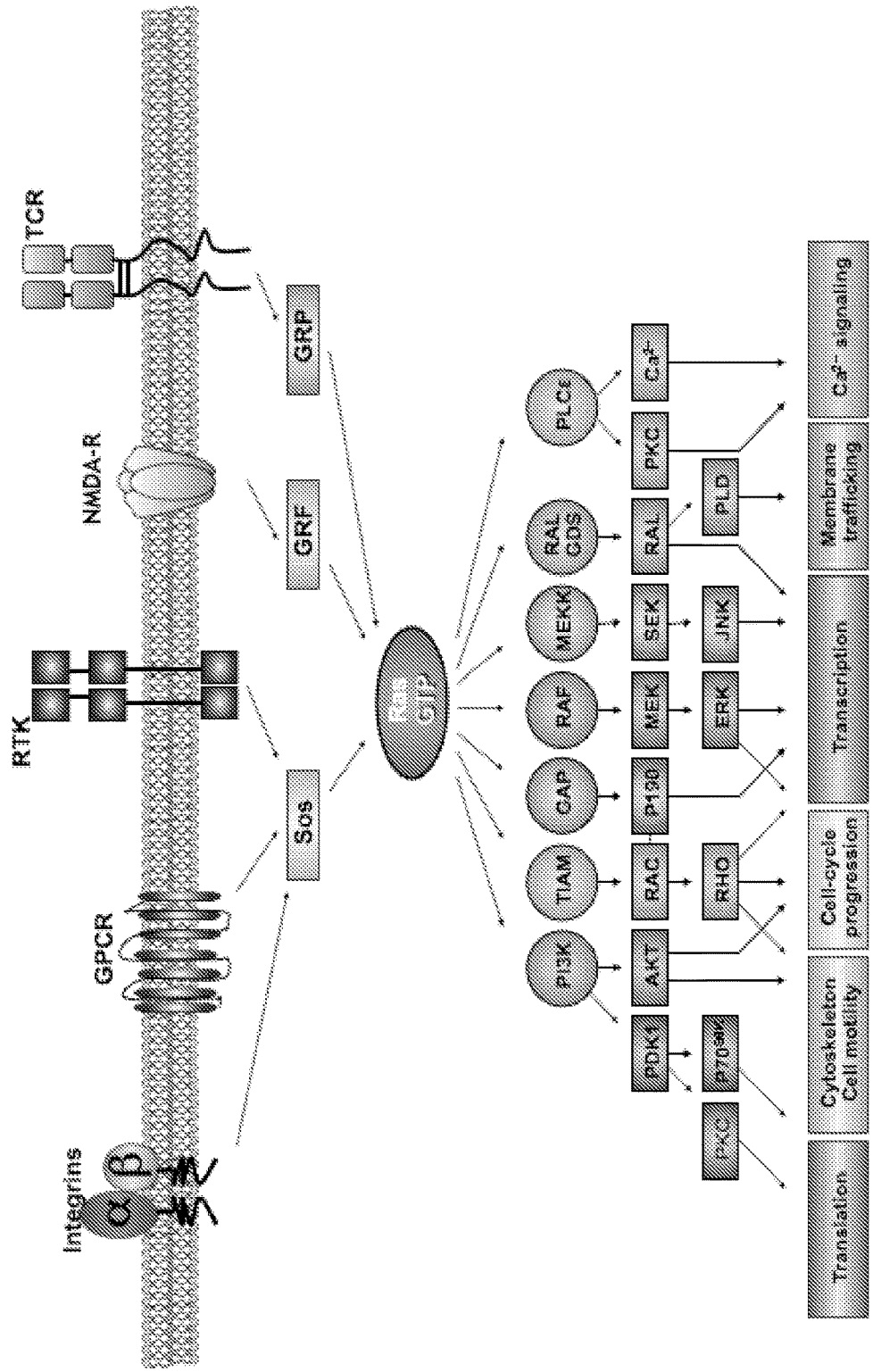
FIG. 1 shows a schematic of the Ras signalling pathway.

The present invention relates to hydrogen bond surrogate ("HBS")-derived α-helices capable of disrupting the Ras signaling pathway. These HBS helices can potentially function as in vivo inhibitors of Ras/Sos interaction.

A first aspect of the present invention relates to a peptide having one or more stable, internally-constrained HBS α-helices, where the peptide mimics at least a portion of a protein capable of interacting with a Ras protein. For example, the peptide mimics an alpha-helical portion of the protein capable of interacting with a Ras protein.

The term "mimic" refers to the ability of a composition of the invention to effect a similar activity as a natural protein such as Sos. A "mimic" encompasses both functional and structural mimics of such proteins. For example, the mimic is a protein which shares a certain percent homology (e.g. 60%, 70%, 80%, 85%, 90%, or 95% homology) with the target protein. Alternatively, the mimic is derived from a different sequence that nevertheless is capable of interacting with Ras in a functionally similar manner, for example by interacting with the same active site.

Peptides according to the invention mimic, for instance, a portion of the sequence of a guanine-nucleotide-exchange factor such as the Sos protein. Other nucleotide exchange factors include Cdc25, Sdc25 and RasGRF. The Sos protein comprises two alpha-helical structural domains, including an N-terminal domain (amino acids 568-741, encompassing α-helices α1 through α6) and a C-terminal domain (amino acids 752-1044, encompassing α-helices αA-αK). The C-terminal domain of the Sos protein is involved primarily in interaction with Ras. In particular, helix αH plays an important role in the nucleotide exchange mechanism.

In some embodiments, suitable peptides of the invention mimic at least one α-helix which is an αA, αB, αC, αD, αE, αF, αG, αH, αI, αJ, or αK helix of Sos. For instance, peptides mimic the αH or α1 helix of Sos. In some embodiments, peptides of the invention mimic amino acids 929 through 944 of the Sos protein.

These artificial α-helices are expected to competitively interfere with Sos helices for binding with Ras, thereby modulating the interaction of Ras and Sos.

By way of example, the artificial α-helices of the present invention can mimic at least a portion of the Sos protein as shown in Table 1.

TABLE 1

Exemplary Ras/Sos Helices.

| Name | Sequence | SEQ ID NO: | Solubility | % Inhibition |
|---|---|---|---|---|
| wt (Sos929-944) | FFGIYLTNILKTEEGN | 2 | insoluble | <10 |
| 1 | FEGIYRTDILRTEEGN | 3 | partially | 13 |
| HBS 1 | FEGIYRTDILRTEEGN | 3 | partially | 11 |
| 2 | FGEGIYRTDILRTEEGN | 4 | partially | <10 |
| 3 | AEGIYRTDILRTEEGN | 5 | partially | <10 |
| 4 | AEGIYRADILRTEEGN | 6 | partially | <10 |
| 5 | FEGIYRTDILR | 7 | soluble | <10 |
| 6 | FEGIYRTELLKAEEAN | 8 | soluble | 20 |
| HBS 6 | FEGIYRTELLKAEEAN | 8 | soluble | 40 |
| 7 | FEGIYRLELLKAEEAN | 9 | soluble | 37 |
| HBS 7 | FEGIYRLELLKAEEAN | 9 | soluble | 64 |
| HBS 7$^{mut}$ | AEGIYRLELLKAEAAA | 10 | soluble | 15 |
| 8 | FEGIYRLELLK | 11 | soluble | <5 |
| HBS 8 | FEGIYRLELLK | 11 | soluble | <5 |
| HBS 9 | FEGLLRLWLRKAibEEAN | 12 | soluble | 35 |
| 10 | FEGLLRLWLRKAibEEAibN | 13 | soluble | 50 |
| HBS 10 | FEGLLRLWLRKAibEEAibN | 13 | soluble | 60 |
| 11 | FEGIYRLELLKAibEEAibN | 14 | soluble | 30 |
| HBS 11 | FEGIYRLELLKAibEEAibN | 14 | soluble | 20 |
| 12 | FEGLLRLWLRKAEEAN | 15 | soluble | 50 |

TABLE 1-continued

Exemplary Ras/Sos Helices.

| Name | Sequence | SEQ ID NO: | Solubility | % Inhibition |
|------|----------|------------|------------|--------------|
| HBS 12 | FEGLLRLWLRKAEEAN | 15 | soluble | 55 |
| 13 | FEAIYRLELLKAEEAN | 16 | soluble | 40 |
| HBS 13 | FEAIYRLELLKAEEAN | 16 | soluble | 50 |
| 15 | FEAIYRLEKLKAEEAN | 17 | soluble | 50 |
| HBS 15^ | FEAIYRLEK*LKAE*EAN | 18 | soluble | <10 |
| HBS 16 | FEGIYRLEKLKAEEANRR | 19 | soluble | 56 |

Design of peptides and HBS helices that mimic Sos929-944 α-H sequence.
"^" refers to peptides containing a lactam-bridge between K* and E* residues (e.g. HBS 15).
"% Inhibition" represents inhibition of the Sos-mediated nucleotide exchange from Ras.
Value is normalized for the exchange of nucleotide from Ras in the presence and absence of Sos.

Design of peptides and FIBS helices that mimic $Sos_{929-944}$ α-H sequence. "^" refers to peptides containing a lactam-bridge between K* and E* residues (e.g. HBS 15). "% Inhibition" represents inhibition of the Sos-mediated nucleotide exchange from Ras. Value is normalized for the exchange of nucleotide from Ras in the presence and absence of Sos.

Generally, suitable peptides of the present invention include those that include the formula:

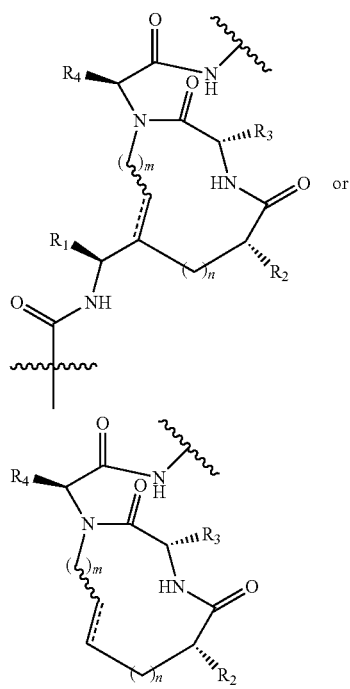

where
------- is a single or double carbon-carbon bond;
∿∿∿∿ is a single bond and is cis or trans when ------- is a double bond;
n is 1 or 2;
m is zero or any positive integer;
$R_1$, $R_2$, $R_3$ and $R_4$ are independently hydrogen, an amino acid side chain, an alkyl group, or an aryl group.

The variable m can be zero or any positive integer, for example 1, 2, 3, 4 or 5. In some embodiments, m is 0, 1 or 2. In some embodiments, m is 0. In other embodiments, m is 1 or 2.

The variable n can be 1 or 2. In other embodiments, n is 1. In still other embodiments, n is 2.

The substituents $R_1$, $R_2$, $R_3$ and $R_4$ are independently hydrogen, an amino acid side chain, an alkyl group, or an aryl group. For example, $R_1$, $R_2$, $R_3$ and $R_4$ are amino acid side chains. In some embodiments, $R_1$, $R_2$, $R_3$ and $R_4$ are naturally occurring amino acid side chains. In other embodiments, at least one amino acid side chain is a nonnaturally occurring side chain.

In some embodiments, $R_3$ is a peptide comprising a sequence of the formula FXGZZXZXZLXZEXXN (SEQ ID NO: 1) where X is any amino acid residue and Z is a hydrophobic residue. In another embodiment, a peptide of the present invention includes an amino acid sequence of Table 1, and has an internally-constrained α-helical region spanning residues 1 through 4 of an amino acid sequence of Table 1.

As will be apparent to one of ordinary skill in the art, the methods of the present invention may be used to prepare peptides having highly stabilized, internally-constrained α-helices. The constraint may be placed anywhere within the peptide, not just at the N-terminus. For example, a compound prepared according to the methods of the present invention may have the formula

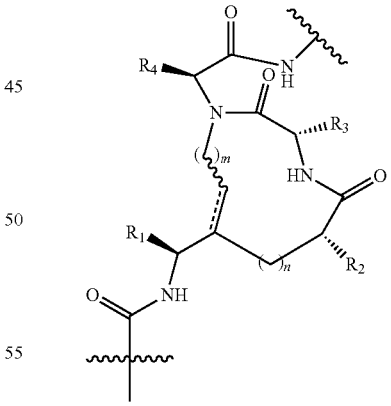

The peptides produced according to the methods of the present invention may, for example, be less than 40, 30, 25, 20, or 15 amino acids, including, for example, less than 10 amino acid residues.

The present invention also relates to peptides having one or more stable, internally-constrained α-helices. The one or more stable, internally-constrained secondary structures includes the following motifs:

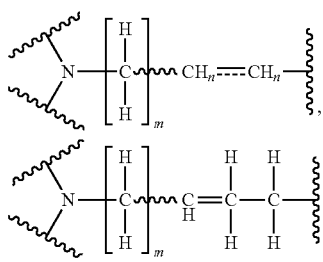

where ⸺ is a single or double bond, ∿∿∿ is a single bond and is cis or trans when ⸺ is a double bond; n is 1 or 2; and m is any number. Examples of such motifs include:

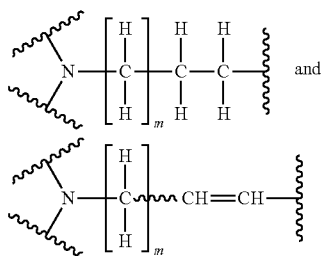

Figure 2:
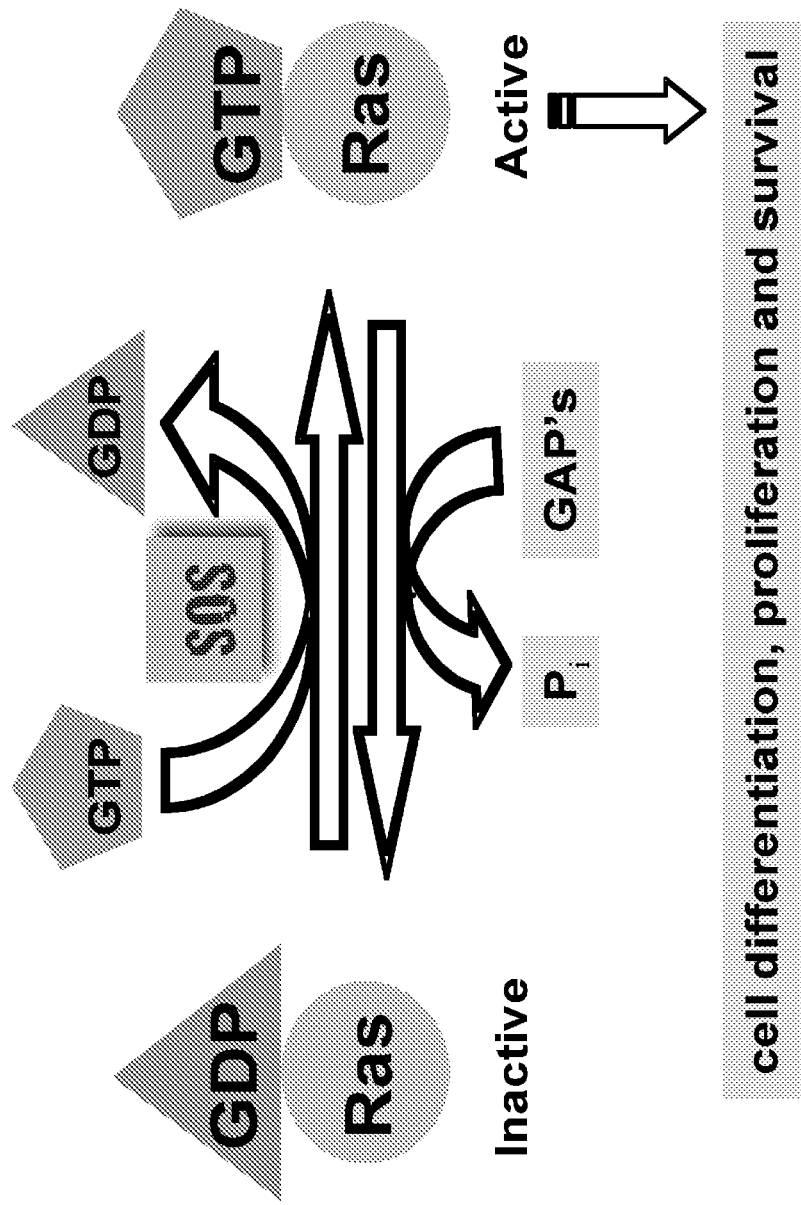
FIG. 2 shows the relationship between Ras and Sos. The activity of Ras is facilitated by the specific guanine nucleotide exchange factor Sos. Activated Ras controls a multitude of signaling transduction pathways.
Figure 3:
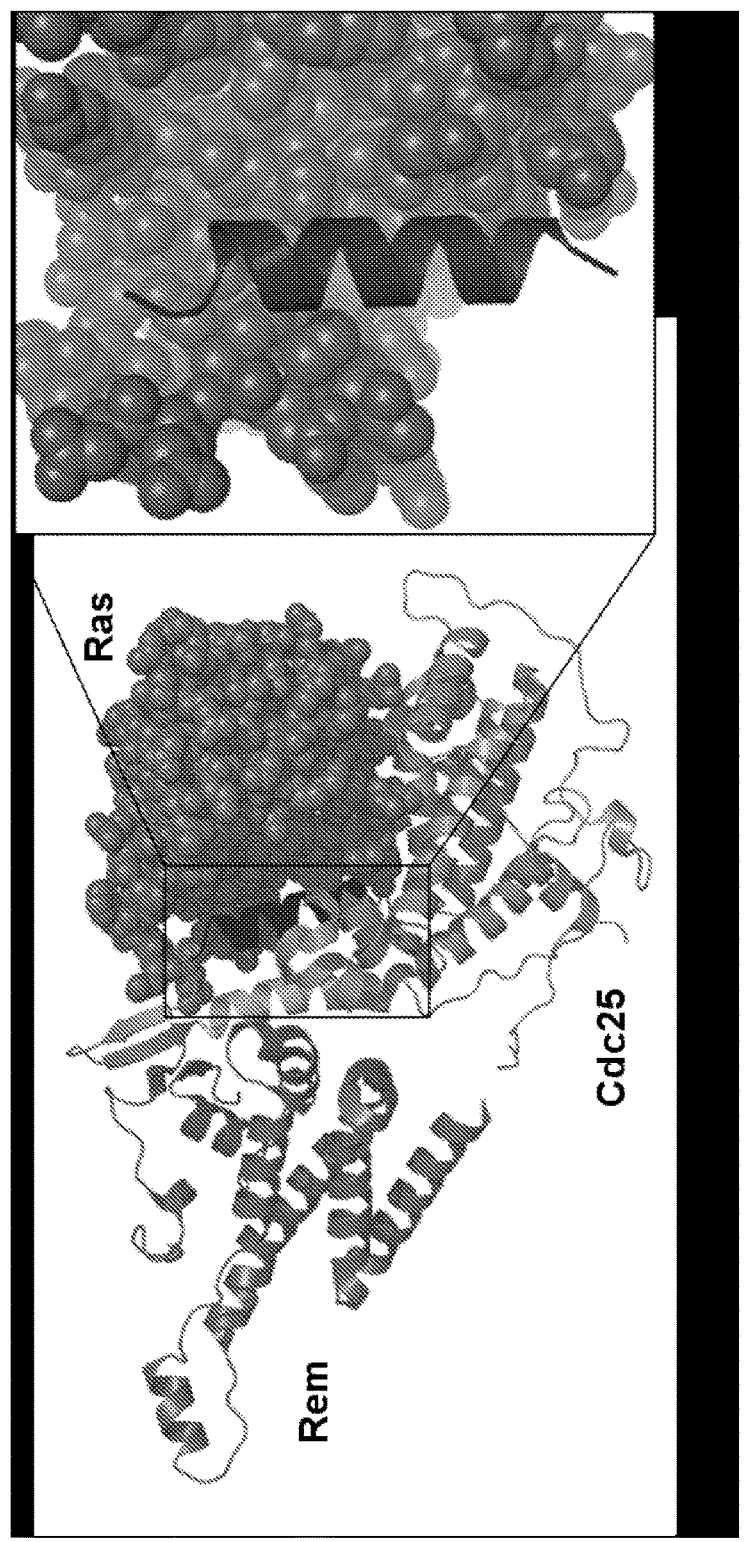
FIG. 3 shows the key α-helical interface between Ras and Sos (PDB accession number 1BKD).

HBS α-helices of the present invention are obtained by replacing an N-terminal main-chain i and i+4 hydrogen bond with a carbon-carbon bond through a ring-closing metathesis reaction, as shown in FIG. 2 (U.S. Pat. No. 7,202,332 to Arora et al.; Chapman & Arora, "Optimized Synthesis of Hydrogen-bond Surrogate Helices: Surprising Effects of Microwave Heating on the Activity of Grubbs Catalysts," *Org. Lett.* 8:5825-8 (2006); Chapman et al., "A Highly Stable Short α-Helix Constrained by a Main-chain Hydrogen-bond Surrogate," *J. Am. Chem. Soc.* 126:12252-3 (2004); Dimartino et al., "Solid-phase Synthesis of Hydrogen-bond Surrogate-derived α-Helices," *Org. Lett.* 7:2389-92 (2005), which are hereby incorporated by reference in their entirety). The hydrogen bond surrogate pre-organizes an α-turn and stabilizes the peptide sequence in an α-helical conformation. HBS α-helices have been shown to adopt stable α-helical conformations from a variety of short peptide sequences (Wang et al., "Evaluation of Biologically Relevant Short α-Helices Stabilized by a Main-chain Hydrogen-bond Surrogate," *J. Am. Chem. Soc.* 128:9248-56 (2006), which is hereby incorporated by reference in its entirety). It has also been shown that these artificial α-helices can target their expected protein receptor with high affinity (Wang et al., "Enhanced Metabolic Stability and Protein-binding Properties of Artificial α Helices Derived from a Hydrogen-bond Surrogate: Application to Bcl-xL," *Angew. Chem. Int'l Ed. Engl.* 44:6525-9 (2005), originally published at *Angew. Chem.* 117:6683-7 (2005), which is hereby incorporated by reference in its entirety).

In another aspect, preparing a compound of the invention involves providing a peptide precursor compound and promoting carbon-carbon bond formation to result in a stable, internally-constrained alpha-helix.

In one embodiment, the precursor has the formula:

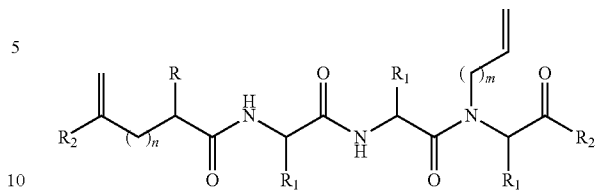

The compound of the formula above may be reacted under conditions effective to promote formation of a carbon-carbon bond. Such a reaction may be, for example, metathesis. The exceptional functional group tolerance displayed by the olefin metathesis catalysts for the facile introduction of non-native carbon-carbon constraints in the preparation of peptidomimetics suggests that X and Y could be two carbon atoms connected through an olefin metathesis reaction, as shown in Scheme 2 (Hoveyda et al., "Ru Complexes Bearing Bidentate Carbenes: From Innocent Curiosity to Uniquely Effective Catalysts for Olefin Metathesis," *Org. Biomolec. Chem.* 2:8-23 (2004); Trnka et al., "The Development of L2X2Tu=CHR Olefin Metathesis Catalysts: An Organometallic Success Story," *Accounts Chem. Res.* 34:18-29 (2001), which are hereby incorporated by reference in their entirety).

This aspect of the present invention may, for example, involve a ring-closing olefin metathesis reaction. An olefin metathesis reaction couples two double bonds (olefins) to afford two new double bonds (one of which is typically ethylene gas). A ring-closing olefin metathesis utilizes an olefin metathesis reaction to form a macrocycle. In this reaction, two double bonds within a chain are connected. The reaction may be performed with a metathesis catalyst, for example of the formula

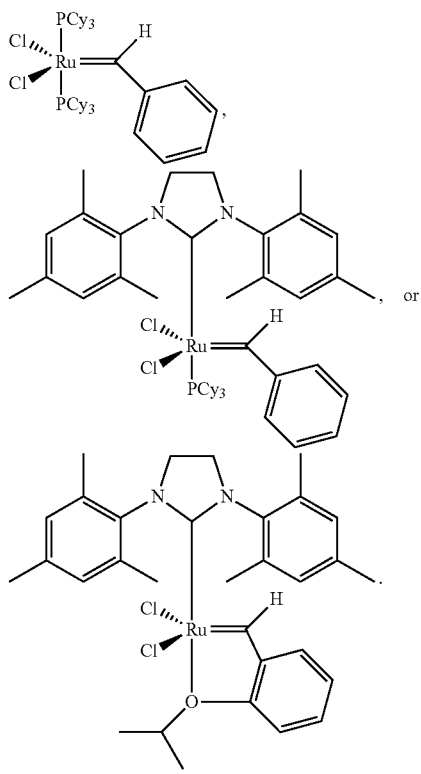

In other embodiments, the metathesis catalyst is of the formula

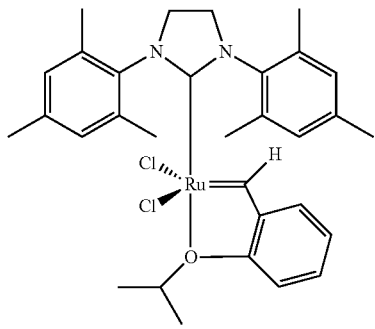

The metathesis reaction may be performed, for example, at a temperature between about 25° C. and 110° C., and more preferably, at a temperature of about 50° C.

The metathesis reaction may be performed with an organic solvent, such as dichloromethane, dichloroethane, trichloroethane, or toluene.

The reactions disclosed herein may, for example, be carried out on a solid support. Suitable solid supports include particles, strands, precipitates, gels, sheets, tubing, spheres, containers, capillaries, pads, slices, films, plates, slides, discs, membranes, etc. These solid supports can be made from a wide variety of materials, including polymers, plastics, ceramics, polysaccharides, silica or silica-based materials, carbon, metals, inorganic glasses, membranes, or composites thereof. The substrate is preferably flat but may take on a variety of alternative surface configurations. For example, the substrate may contain raised or depressed regions on which the synthesis takes place. The substrate and its surface preferably form a rigid support on which to carry out the reactions described herein. Other substrate materials will be readily apparent to those of ordinary skill in the art upon review of this disclosure.

The metathesis reaction performed may initially yield a compound in which the newly formed carbon-carbon bond is a double bond. This double bond can be subsequently converted to a single bond by hydrogenation methods known in the art.

In another aspect, the invention provides a method of inhibiting Ras signaling in a cell, comprising contacting the cell with an effective amount of a composition comprising a peptide having a stable, internally-constrained alpha-helix, wherein said alpha helix is constrained by a crosslink formed by a carbon-carbon bond-forming reaction, and further wherein the peptide mimics at least a portion of a protein capable of interacting with a Ras protein. In some embodiments, the cell is in a living organism. The cell may be, for example, a cancer cell such as a liquid or solid tumor cell. The invention further provides a method of treating cancer in a subject in need thereof, comprising administering to the subject a peptide having a stable, internally-constrained alpha-helix, wherein said alpha helix is constrained by a crosslink formed by a carbon-carbon bond-forming reaction, and further wherein the peptide mimics at least a portion of a protein capable of interacting with a Ras protein.

As will be apparent to one of ordinary skill in the art, administering may be carried out using generally known methods.

Administration can be accomplished either via systemic administration to the subject or via targeted administration to affected cells. Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, by application to mucous membranes (such as that of the nose, throat, bronchial tubes, genitals, and/or anus), or implantation of a sustained release vehicle.

Typically, the peptide of the present invention will be administered to a mammal as a pharmaceutical formulation that includes the therapeutic agent and any pharmaceutically acceptable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers and/or excipients. The amount of active compound in such therapeutically useful compositions is such that a suitable dosage unit will be obtained.

The agents may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

The agents may also be administered parenterally. Solutions or suspensions of the agent can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The agents of the present invention may be administered directly to a targeted tissue, e.g., tissue that is susceptible to the condition to be treated. Additionally and/or alternatively, the agent may be administered to a non-targeted area along with one or more agents that facilitate migration of the agent to (and/or uptake by) a targeted tissue, organ, or cell. As will be apparent to one of ordinary skill in the art, the therapeutic agent itself be modified to facilitate its transport to (and uptake by) the desired tissue, organ, or cell.

Exemplary delivery devices include, without limitation, nebulizers, atomizers, liposomes, transdermal patches, implants, implantable or injectable protein depot compositions, and syringes. Other delivery systems which are known to those of skill in the art can also be employed to achieve the desired delivery of the therapeutic agent to the desired organ, tissue, or cells in vivo to effect this aspect of the present invention.

Any suitable approach for delivery of the agents can be utilized to practice this aspect of the present invention. Typically, the agent will be administered to a patient in a vehicle that delivers the agent(s) to the target cell, tissue, or organ.

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner where the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987), which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., each of which is hereby incorporated by reference in its entirety.

These liposomes can be produced such that they contain, in addition to the therapeutic agents of the present invention, other therapeutic agents, such as anti-inflammatory agents, which would then be released at the target site (e.g., Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), which is hereby incorporated by reference in its entirety).

An alternative approach for delivery of proteins or polypeptide agents (e.g., peptides of the present invention) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins according to U.S. Pat. No. 5,817,789 to Heartlein et al., which is hereby incorporated by reference in its entirety. The chimeric protein can include a ligand domain and the polypeptide agent (e.g., the artificial α-helix of the present invention). The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein.

Administration can be carried out as frequently as required and for a duration that is suitable to provide effective treatment. For example, administration can be carried out with a single sustained-release dosage formulation or with multiple daily doses.

The amount to be administered will, of course, vary depending upon the treatment regimen. Generally, an agent is administered to achieve an amount effective for an improvement in the state of the patient (i.e., a therapeutically effective amount). Thus, in the case of cancer, a therapeutically effective amount can be an amount which is capable of at least partially decreasing the size of a tumor, decreasing the number of cancerous cells in the body, or slowing the increase in number of cancer cells in the body. The dose required to obtain an effective amount may vary depending on the agent, formulation, cancer, and individual to whom the agent is administered.

Determination of effective amounts may also involve in vitro assays in which varying doses of agent are administered to cells in culture and the concentration of agent effective for inhibiting growth of cancer cells is determined in order to calculate the concentration required in vivo. Effective amounts may also be based on in vivo animal studies. A therapeutically effective amount can be determined empirically by those of skill in the art.

Methods of Treatment

In some embodiments, the compounds of the invention is used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth. Examples of non-pathologic hyperproliferative cells include proliferation of cells associated with wound repair. Examples of cellular proliferative and/or differentiative disorders include cancer, e.g., carcinoma, sarcoma, or metastatic disorders. In some embodiments, the compounds are novel therapeutic agents for controlling breast cancer, ovarian cancer, colon cancer, lung cancer, metastasis of such cancers and the like.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991), *Crit Rev. Oncol/Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

In some embodiments, the peptides of the invention are used to treat a cancer mediated by a mutated Ras protein. Cancers known to frequently involve such mutations include, but are not limited to, non-small-cell lung cancer (adenocarcinoma), colorectal cancer, pancreatic cancer, thyroid cancers (e.g. follicular, undifferentiated papillary or papillary), seminoma, melanoma, bladder cancer, liver cancer, kidney cancer, myelodysplastic syndrome, and acute myelogenous leukemia.

Breast Cancer

In one aspect, the invention provides methods of treating breast cancer by administering the compounds of the invention. Breast cancer includes invasive breast carcinomas, such as invasive ductal carcinoma, invasive lobular carcinoma, tubular carcinoma, invasive cribriform carcinoma, medullary carcinoma, mucinous carcinoma and other tumours with abundant mucin, cystadenocarcinoma, columnar cell mucinous carcinoma, signet ring cell carcinoma, neuroendocrine tumours (including solid neuroendocrine carcinoma, atypical carcinoid tumour, small cell/oat cell carcinoma, or large cell neuroendocrine carcioma), invasive papillary carcinoma, invasive micropapillary carcinoma, apocrine carcinoma, metaplastic carcinomas, pure epithelial metaplastic carciomas, mixed epithelial/mesenchymal metaplastic carcinomas, lipid-rich carcinoma, secretory carcinoma, oncocytic carcinoma, adenoid cystic carcinoma, acinic cell carcinoma, glycogen-rich clear cell carcinoma, sebaceous carcinoma, inflammatory carcinoma or bilateral breast carcinoma; mesenchymal tumors such as haemangioma, angiomatosis, haemangiopericytoma, pseudoangiomatous stromal hyperplasia, myofibroblastoma, fibromatosis (aggressive), inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma, or leiomysarcoma; myoepithelial lesions such as myoepitheliosis, adenomyoepithelial adenosis, adenomyoepithelioma, or malignant myoepithelioma; fibroepithelial tumours such as fibroadenoma, phyllodes tumour, low grade periductal stromal sarcoma, or mammary hamartoma; and tumours of the nipple such as nipple adenoma, syringomatous adenoma, or Paget's disease of the nipple.

Treatment of breast cancer may be effected in conjunction with any additional therapy, such as a therapy that is part of the standard of care. A surgical technique such as lumpectomy or mastectomy may be performed prior to, during, or following treatment with the compounds of the invention. Alternatively, radiation therapy may be used for the treatment of breast cancer in conjunction with the compounds of the invention. In other cases, the compounds of the invention are administered in combination with a second therapeutic agent. Such an agent may be a chemotherapeutic agent such as an individual drug or combination of drugs and therapies. For example, the chemotherapeutic agent can be an adjuvant chemotherapeutic treatment such as CMF (cyclophosphamide, methotrexate, and 5-fluorouracil); FAC or CAF (5-fluorouracil, doxorubicin, cyclophosphamide); AC or CA (doxorubicin and cyclophosphamide); AC-Taxol (AC followed by paclitaxel); TAC (docetaxel, doxorubicin, and cyclophosphamide); FEC (5-Fluorouracil, epirubicin and cyclophosphamide); FECD (FEC followed by docetaxel); TC (docetaxel and cyclophosphamide). In addition to chemotherapy, trastuzumab may also be added to the regimen depending on the tumor characteristics (i.e. HER2/neu status) and risk of relapse. Hormonal therapy may also be appropriate before, during or following chemotherapeutic treatment. For example, tamoxifen may be administered or a compound in the category of aromatase inhibitors including, but not limited to aminogluthetimide, anastrozole, exemestane, formestane, letrozole, or vorozole. In other embodiments, an antiangiogenic agent may be used in combination therapy for the treatment of breast cancer. The antiangiogenic agent may be an anti-VEGF agent including, but not limited to bevacizumab.

Ovarian Cancer

In another aspect, the compounds of the invention may be used to treat ovarian cancer. Ovarian cancers include ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The compounds of the invention may be administered in conjunction with a second therapy such as a therapy that is part of the standard of care. Surgery, immunotherapy, chemotherapy, hormone therapy, radiation therapy, or a combination thereof are some possible treatments available for ovarian cancer. Some possible surgical procedures include debulking, and a unilateral or bilateral oophorectomy and/or a unilateral or bilateral salpigectomy.

Anti-cancer drugs that may be used include cyclophosphamide, etoposide, altretamine, and ifosfamide. Hormone therapy with the drug tamoxifen may be used to shrink ovarian tumors. Radiation therapy may be external beam radiation therapy and/or brachytherapy.

Prostate Cancer

In another aspect, the compounds of the invention may be used to treat prostate cancer. Prostate cancers include adenocarcinomas and metastasized adenocarcinomas. The compounds of the invention may be administered in conjunction with a second therapy such as a therapy that is pail of the standard of care. Treatment for prostate cancer may involve surgery, radiation therapy, High Intensity Focused Ultrasound (HIFU), chemotherapy, cryosurgery, hormonal therapy, or any combination thereof. Surgery may involve prostatectomy, radical perineal prostatectomy, laparoscopic radical prostatectomy, transurethral resection of the prostate or orchiectomy. Radiation therapy may include external beam radiation therapy and/or brachytherapy. Hormonal therapy may include orchiectomy; administration of antiandrogens such as flutamide, bicalutamide, nilutamide, or cyproterone acetate; medications which inhibit the production of adrenal androgens such as DHEA, such as ketoconazole and aminoglutethimide; and GnRH antagonists or agonists such as Abarelix (Plenaxis®), Cetrorelix (Cetrotide®), Ganirelix (Antagon®), leuprolide, goserelin, triptorelin, or buserelin. Treatment with an anti-androgen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB). Chemotherapy includes, but is not limited to, administration of docetaxel, for example with a corticosteroid such as prednisone. Anti-cancer drugs such as doxorubicin, estramustine, etoposide, mitoxantrone, vinblastine, paclitaxel, carboplatin may also be administered to slow the growth of prostate cancer, reduce symptoms and improve the quality of life. Additional compounds such as bisphosphonate drugs may also be administered.

Renal Cancer

In another aspect, the compounds of the invention may be used to treat renal cancer. Renal cancers include, but are not limited to, renal cell carcinomas, metastases from extrarenal primary neoplasms, renal lymphomas, squamous cell carcinomas, juxtaglomerular tumors (reninomas), transitional cell carcinomas, angiomyolipomas, oncocytomas and Wilm's tumors. The compounds of the invention may be administered in conjunction with a second therapy such as a therapy that is part of the standard of care. Treatment for renal cancer may involve surgery, percutaneous therapies, radiation therapies, chemotherapy, vaccines, or other medication. Surgical techniques useful for treatment of renal cancer in combination with the compounds of the invention include nephrectomy, which may include removal of the adrenal gland, retroperitoneal lymph nodes, and any other surrounding tissues affected by the invasion of the tumor. Percutaneous therapies include, for example, image-guided therapies which may involve imaging of a tumor followed by its targeted destruction by radiofrequency ablation or cryotherapy. In some cases, other chemotherapeutic or other medications useful in treating renal cancer may be alpha-interferon, interleukin-2, bevacizumab, sorafenib, sunitib, temsirolimus or other kinase inhibitors.

Pancreatic Cancer

In other aspects, the invention provides methods of treating pancreatic cancer by administering compounds of the invention, such as a pancreatic cancer selected from the following: an epitheliod carcinoma in the pancreatic duct tissue and an adenocarcinoma in a pancreatic duct. The most common type of pancreatic cancer is an adenocarcinoma, which occurs in the lining of the pancreatic duct. Possible treatments available for pancreatic cancer include surgery, immunotherapy, radiation therapy, and chemotherapy. Possible surgical treatment options include a distal or total pancreatectomy and a pancreaticoduodenectomy (Whipple procedure). Radiation therapy may be an option for pancreatic cancer patients, specifically external beam radiation where radiation is focused on the tumor by a machine outside the body. Another option is intraoperative electron beam radiation administered during an operation. Chemotherapy may also be used to treat pancreatic cancer patients. Suitable anti-cancer drugs include, but are not limited to, 5-fluorouracil (5-FU), mitomycin, ifosfamide, doxorubicin, streptozocin, chlorozotocin, and combinations thereof. The methods provided by the invention can provide a beneficial effect for pancreatic cancer patients, by administration of a polypeptide of the invention or a combination of administration of a compound and surgery, radiation therapy, or chemotherapy.

Colon Cancer

In one aspect, compounds of the invention may be used for the treatment of colon cancer, including but not limited to non-neoplastic polyps, adenomas, familial syndromes, colorectal carcinogenesis, colorectal carcinoma, and carcinoid tumors. Possible treatments available for colon cancer that may be used in conjunction with the compounds of the invention include surgery, chemotherapy, radiation therapy or targeted drug therapy.

Radiation therapy may include external beam radiation therapy and/or brachytherapy. Chemotherapy may be used to reduce the likelihood of metastasis developing, shrink tumor size, or slow tumor growth. Chemotherapy is often applied after surgery (adjuvant), before surgery (neo-adjuvant), or as the primary therapy if surgery is not indicated (palliative). For example, exemplary regimens for adjuvant chemotherapy involve the combination of infusional 5-fluorouracil, leucovorin, and oxaliplatin (FOLFOX). First line chemotherapy regimens may involve the combination of infusional 5-fluorouracil, leucovorin, and oxaliplatin (FOLFOX) with a targeted drug such as bevacizumab, cetuximab or panitumumab or infusional 5-fluorouracil, leucovorin, and irinotecan (FOLFIRI) with targeted drug such as bevacizumab, cetuximab or panitumumab. Other chemotherapeutic agents that may be useful in the treatment or prevention of colon cancer in combination with the compounds of the invention are Bortezomib (Velcade®), Oblimersen (Genasense®, G3139), Gefitinib and Erlotinib (Tarceva®) and Topotecan (Hycamtin®).

Lung Cancer

Some embodiments provide methods for the treatment of lung cancer using the compounds of the invention. Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer, e.g. small cell lung carcinomas, accounts for 15-20% of lung cancers. Treatment options for lung cancer include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy may be external beam radiation therapy or brachytherapy. Some anti-cancer drugs that may be used in chemotherapy to treat lung cancer in combination with the compounds of the invention include cisplatin, carboplatin, paclitaxel, docetaxel, gemcitabine, vinorelbine, irinotecan, etoposide, vinblastine, gefitinib, ifosfamide, methotrexate, or a combination thereof. Photodynamic therapy (PDT) may be used to treat lung cancer patients. The methods described herein can provide a beneficial effect for lung cancer patients, by administration of a compound or a combination of administration of a compound and surgery, radiation therapy, chemotherapy, photodynamic therapy, or a combination thereof.

Examples of cellular proliferative and/or differentiative disorders of the liver include, but are not limited to, nodular hyperplasias, adenomas, and malignant tumors, including primary carcinoma of the liver and metastatic tumors.

Immunoproliferative Disorders

Immunoproliferative disorders (also known as "immunoproliferative diseases" or "immunoproliferative neoplasms") are disorders of the immune system that are characterized by the abnormal proliferation of the primary cells of the immune system, which includes B cells, T cells and Natural Killer (NK) cells, or by the excessive production of immunoglobulins (also known as antibodies). Such disorders include the general categories of lymphoproliferative disorders, hypergammaglobulinemias, and paraproteinemias. Examples of such disorders include, but are not limited to, X-linked lymphoproliferative disorder, autosomal lymphoproliferative disorder, Hyper-IgM syndrome, heavy chain disease, and cryoglobulinemia. Other immunoproliferative disorders can be graft versus host disease (GVHD); psoriasis; immune disorders associated with graft transplantation rejection; T cell lymphoma; T cell acute lymphoblastic leukemia; testicular angiocentric T cell lymphoma; benign lymphocytic angiitis; and autoimmune diseases such as lupus erythematosus, Hashimoto's thyroiditis, primary myxedema, Graves' disease, pernicious anemia, autoimmune atrophic gastritis, Addison's disease, insulin dependent diabetes mellitus, good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatoid arthritis, polymyositis, scleroderma, and mixed connective tissue disease.

Combination Treatments

In one embodiment, compounds of the invention may be used for the treatment of cancer in conjunction with alkylating and alkylating-like agents. Such agents include, for example, nitrogen mustards such as chlorambucil, chlormethine, cyclophosphamide, ifosfamide, and melphalan; nitrosoureas such as carmustine, fotemustine, lomustine, and streptozocin; platinum therapeutic agents such as carboplatin, cisplatin, oxaliplatin, BBR3464, and satraplatin; or other agents, including but not limited to busulfan, dacarbazine, procarbazine, temozolomide, thiotepa, treosulfan, or uramustine.

In another embodiment, compounds of the invention may be used in conjunction with an antineoplastic agent which is an antimetabolite. For example, such an antineoplastic agent may be a folic acid such as aminopterin, methotrexate, pemetrexed, or raltitrexed. Alternatively, the antineoplastic agent may be a purine, including but not limited to cladribine, clofarabine, fludarabine, mercaptopurine, pentostatin, thioguanine. In further embodiments, the antineoplastic agent may be a pyrimidine such as capecitabine, cytarabine, fluorouracil, floxuridine, and gemcitabine.

In still other embodiments, compounds of the invention may be used in conjunction with an antineoplastic agent which is an spindle poison/mitotic inhibitor. Agents in this category include taxanes, for example docetaxel and paclitaxel; and vinca alkaloids such as vinblastine, vincristine, vindesine, and vinorelbine. In yet other embodiments, compounds of the invention may be used in combination with an antineoplastic agent which is a cytotoxic/antitumor antibiotic from the anthracycline family such as daunorubicin, doxorubicin, epirubicin, idarubicin, mitoxantrone, pixantrone, or valrubicin; an antibiotic from the streptomyces family such as actinomycin, bleomycin, mitomycin, or plicamycin; or hydroxyurea. Alternatively, agents used for combination therapy may be topoisomerase inhibitors including, but not limited to camptothecin, topotecan, irinotecan, etoposide, or teniposide.

Alternatively, the antineoplastic agent may be an antibody or antibody-derived agent. For example, a receptor tyrosine kinase-targeted antibody such as cetuximab, panitumumab, or trastuzumab may be used Alternatively, the antibody may be an anti-CD20 antibody such as rituximab or tositumomab, or any other suitable antibody including but not limited to alemtuzumab, bevacizumab, and gemtuzumab. In other embodiments, the antineoplastic agent is a photosensitizer such as aminolevulinic acid, methyl aminolevulinate, porfimer sodium, or verteporfin. In still other embodiments, the antineoplastic agent is a tyrosine kinase inhibitor such as dediranib, dasatinib, erlotinib, gefitinib, imatinib, lapatinib, nilotinib, sorafenib, sunitinib, or vandetanib. Other neoplastic agents suitable in the use of the invention include, for example, alitretinoin, tretinoin, altretamine, amsacrine, anagrelide, arsenic trioxide, asparaginase (pegaspargase), bexarotene, bortezomib, denileukin diftitox, estramustine, ixabepilone, masoprocol, or mitotane.

In other or further embodiments, the compounds described herein are used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, and myelodysplasia.

In other or further embodiments, the compounds of the invention that act to decrease apoptosis are used to treat disorders associated with an undesirable level of cell death. Thus, in some embodiments, the anti-apoptotic compounds of the invention are used to treat disorders such as those that lead to cell death associated with viral infection, e.g., infection associated with infection with human immunodeficiency virus (HIV). A wide variety of neurological diseases are characterized by the gradual loss of specific sets of neurons, and the anti-apoptotic compounds of the invention are used, in some embodiments, in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Other Methods of Use

In other or further embodiments, the anti-apoptotic compounds of the invention are used to treat all such disorders associated with undesirable cell death.

Some examples of immunologic disorders that are treated with the compounds described herein include but are not limited to organ transplant rejection, arthritis, lupus, IBD, Crohn's disease, asthma, multiple sclerosis, diabetes, etc.

Some examples of neurologic disorders that are treated with the compounds described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a prion-mediated disease, and Huntington's Disease.

Some examples of endocrinologic disorders that are treated with the compounds described herein include but are not limited to diabetes, hypothyroidism, hypopituitarism, hypoparathyroidism, hypogonadism, etc.

Examples of cardiovascular disorders (e.g., inflammatory disorders) that are treated or prevented with the compounds of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

EXAMPLES

Example 1—Synthesis of Peptides 1-17

Peptides 1-17 were synthesized as shown in FIGS. 12-15. Resin bound free amine peptides were synthesized by conventional Fmoc solid-phase chemistry on Rink Amide or Knorr resin (loading=0.4 mmole/g) on a CEM Liberty Microwave Peptide Synthesizer. Standard Fmoc amino acids (and 4-petenoic acid) (5 equiv) were activated with HBTU (4.9 equiv) in 6% DIPEA/NMP solution for 15 min and added to the resin bound free amine. The resulting mixture was shaken for 60 minutes. The coupling efficiency was monitored by the ninhydrin test. Fmoc groups were deprotected by treatment with 20% piperidine in NMP (2×20 min). The bis-olefin peptide containing resin was thoroughly washed with DMF and DCM respectively, and dried under vacuum overnight.

Microwave-assisted ring-closing metathesis reactions on resin-bound bis-olefins were performed with the Hoveyda-Grubbs catalyst (0.15 equiv.) in dichloroethane as described in Chapman & Arora, "Optimized Synthesis of Hydrogen-bond Surrogate Helices: Surprising Effects of Microwave Heating on the Activity of Grubbs Catalysts," *Org. Lett.* 8:5825-8 (2006), which is hereby incorporated by reference in its entirety. The reaction mixture was irradiated with these settings: 250 W maximum power, 120° C., 5 minute ramp time, and 10 minute hold time. Resin bound peptides were cleaved from the resin by treatment with a cleavage cocktail ($CF_3CO_2H$:$H_2O$:triisopropylsilane, 95:2.5:2.5) for 1.5 hours, and purified by reversed-phase HPLC.

Several peptides of the invention were examined using liquid chromatography-mass spectrometry ("LCMS"). LCMS data were obtained on an Agilent 1100 series. The LCMS results are shown in Table 2.

TABLE 2

Mass spectrometry results for Peptides 1-12 (LC/MSD (XCT) electrospray trap).

| Name | Sequence | SEQ ID NO: | Mass Calculated $[M]^+$ | Mass Observed $[M]^+$ |
|---|---|---|---|---|
| wt (Sos929-944) | FFGIYLTNILKTEEGN | 2 | 1900.1 | 1900.2 |
| 1 | FEGIYRTDILRTEEGN | 3 | 1954.1 | 1955.1 |
| HBS 1 | FEGIYRTDILRTEEGN | 3 | 2006.1 | 1003.7 |
| 2 | FGEGIYRTDILRTEEGN | 4 | 2011.1 | 2012.1 |
| 3 | AEGIYRTDILRTEEGN | 5 | 1878.0 | 1878.1 |
| 4 | AEGIYRADILRTEEGN | 6 | 1847.9 | 924.9* |
| 5 | FEGIYRTDILR | 7 | 1423.6 | 1423.3 |
| 6 | FEGIYRTELLKAEEAN | 8 | 1924.1 | 1924.1 |
| HBS 6 | FEGIYRTELLKAEEAN | 8 | 1976.1 | 1978.2 |
| 7 | FEGIYRLELLKAEEAN | 9 | 1936.1 | 968.7 |
| HBS 7 | FEGIYRLELLKAEEAN | 9 | 1988.2 | 1989.9 |
| HBS $7^{mut}$ | AEGIYRLELLKAEAAA | 10 | 1811.0 | 1813.3 |
| 8 | FEGIYRLELLK | 11 | 1422.6 | 711.6* |
| HBS 8 | FEGIYRLELLK | 11 | 1473.7 | 1474.9 |
| 9 | FEGLLRLWLRKAibEEAN | 12 | 2014.3 | 672.2** |
| HBS 9 | FEGLLRLWLRKAibEEAN | 12 | 2052.3 | 684.9** |
| 10 | FEGLLRLWLRKAibEEAibN | 13 | 2014.3 | 672.4** |
| HBS 10 | FEGLLRLWLRKAibEEAibN | 13 | 2066.4 | 689.7** |
| 11 | FEGIYRLELLKAibEEAibN | 14 | 1964.2 | 1965.1 |
| HBS 11 | FEGIYRLELLKAibEEAibN | 14 | 2016.2 | 1009.1* |
| 12 | FEGLLRLWLRKAEEAN | 15 | 1986.2 | 993.4* |
| HBS 12 | FEGLLRLWLRKAEEAN | 15 | 2038.3 | 1019.5* |
| 13 | FEAIYRLELLKAEEAN | 16 | 1950.1 | 975.6* |

TABLE 2-continued

Mass spectrometry results for Peptides 1-12
(LC/MSD (XCT) electrospray trap).

| Name | Sequence | SEQ ID NO: | Mass Calculated [M]+ | Mass Observed [M]+ |
|---|---|---|---|---|
| HBS 13 | FEAIYRLELLKAEEAN | 16 | 2001.2 | 2003.0 |
| 15 | FEAIYRLEKLKAEEAN | 17 | 1965.2 | 1966.1 |
| HBS 15 | FEAIYRLEK#LKAE#EAN | 18 | 1999.2 | 2000.1 |
| HBS 16 | FEGIYRLEKLKAEEANRR | 19 | 2343.6 | 2346.0 |

In Table 2,
represents a lactam bridge between the lysine and glutamic acid residues.
*represents [M]$^{2+}$ and ** represents [M]$^{3+}$.

Fluoresceinated versions of exemplary HBS peptides of the invention were also prepared and are shown below:

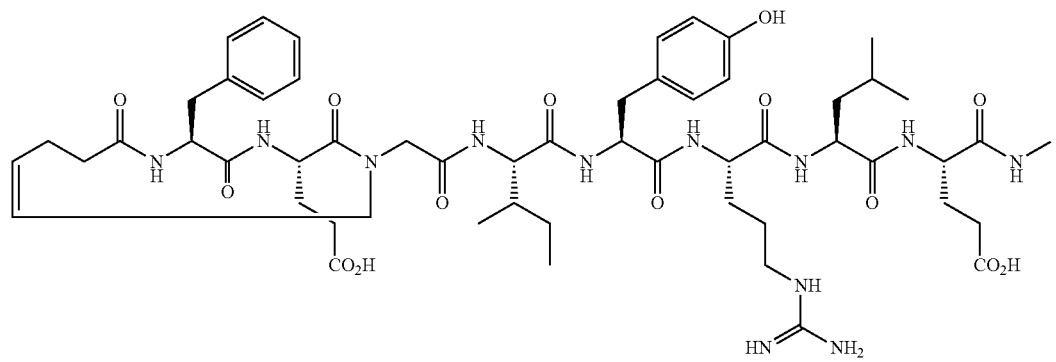

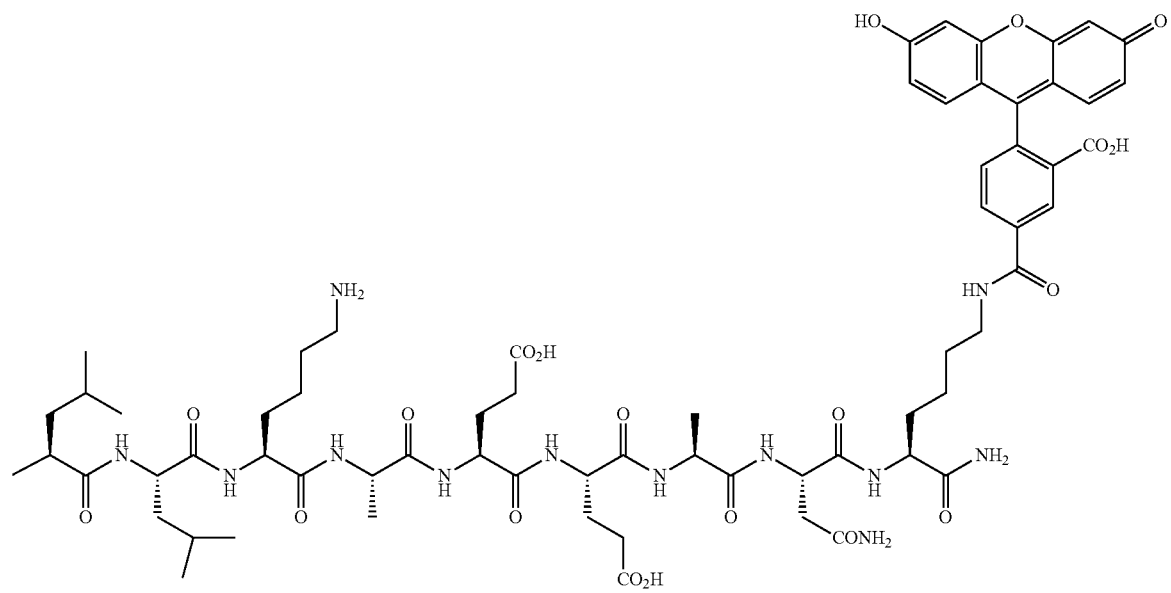

HBS 7 - Flu

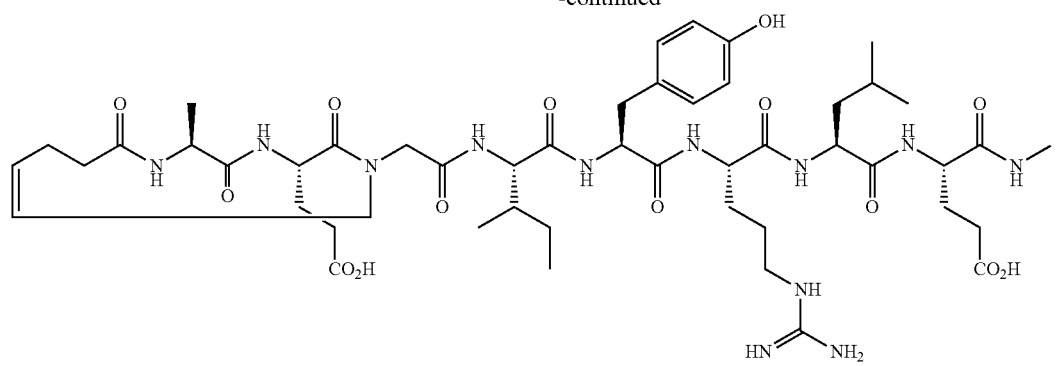
-continued
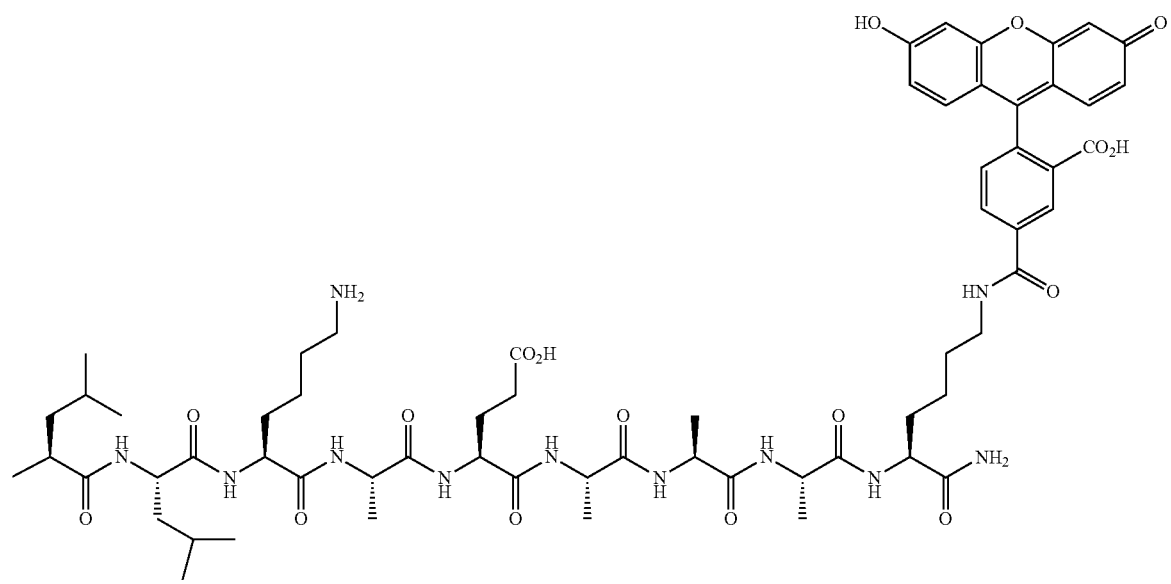
HBS 7$^{mut}$ - Flu
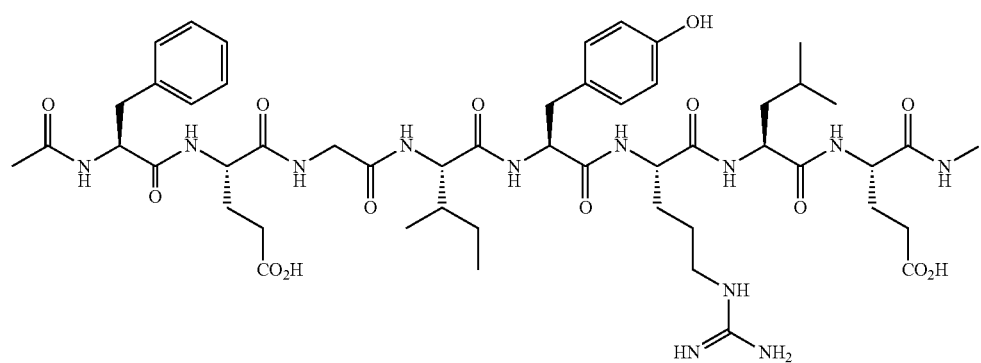

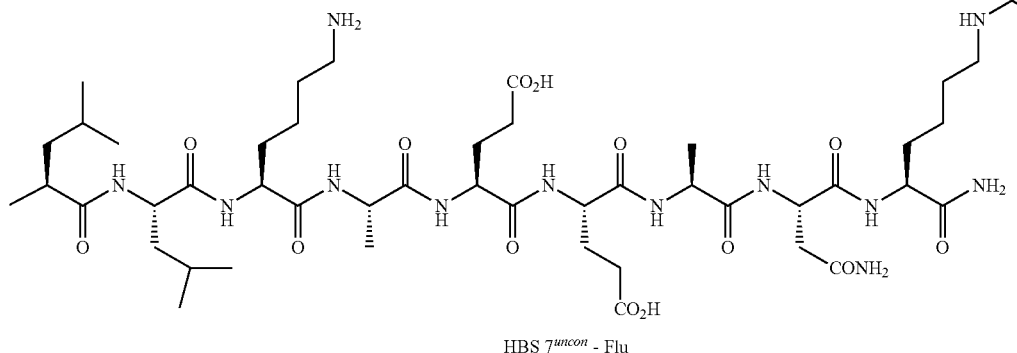

HBS 7$^{uncon}$ - Flu

Example 2—Circular Dichroism Spectroscopy

Figure 9:
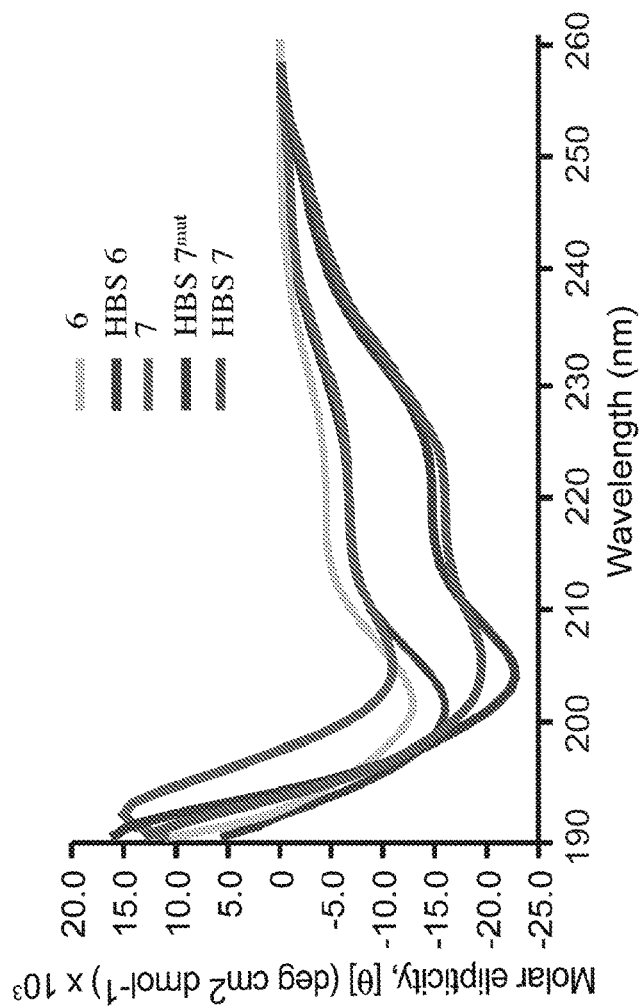
FIG. 9 shows circular dichroism spectra and helicity of HBS peptides.

CD spectra shown in FIG. 9 were recorded on an AVIV 202SF CD spectrometer equipped with a temperature controller using 1 mm length cells and a scan speed of 5 nm/min. The spectra were averaged over 10 scans with the baseline subtracted from analogous conditions as that for the samples. Samples were prepared in 0.1× phosphate buffered saline (13.7 mM NaCl, 1 mM phosphate, 0.27 mM KCl, pH 7.4), containing 10% trifluoroethanol, with the final peptide concentration of 50-100 µM. The concentrations of unfolded peptides were determined by the UV absorption of the tyrosine residue at 276 nm in 6.0 M guanidinium hydrochloride aqueous solution. The helix content of each peptide was determined from the mean residue CD at 222 nm, $[\theta]_{222}$ (deg cm$^2$ dmol$^{-1}$) corrected for the number of amino acids. Percent helicity was calculated from the ratio $[\theta]_{222}/[\theta]_{max}$, where $[\theta]_{max}=(-44000+250T)(1-k/n)$, with k=4.0 and n=number of residues. For details on $\theta_{max}$ calculations for HBS helices, see Wang et al., "Evaluation of Biologically Relevant Short α-Helices Stabilized by a Main-chain Hydrogen-bond Surrogate," J. Am. Chem. Soc. 128:9248-56 (2006), which is hereby incorporated by reference in its entirety.

Figure 10:
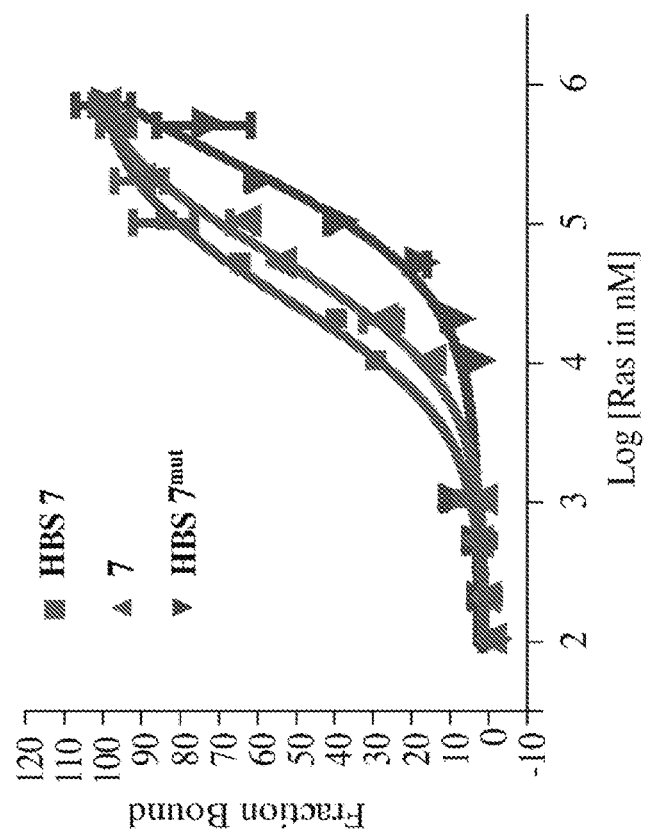
FIG. 10 shows the binding affinity of HBS peptides for Ras as determined by a fluorescence polarization assay.
Figure 11:
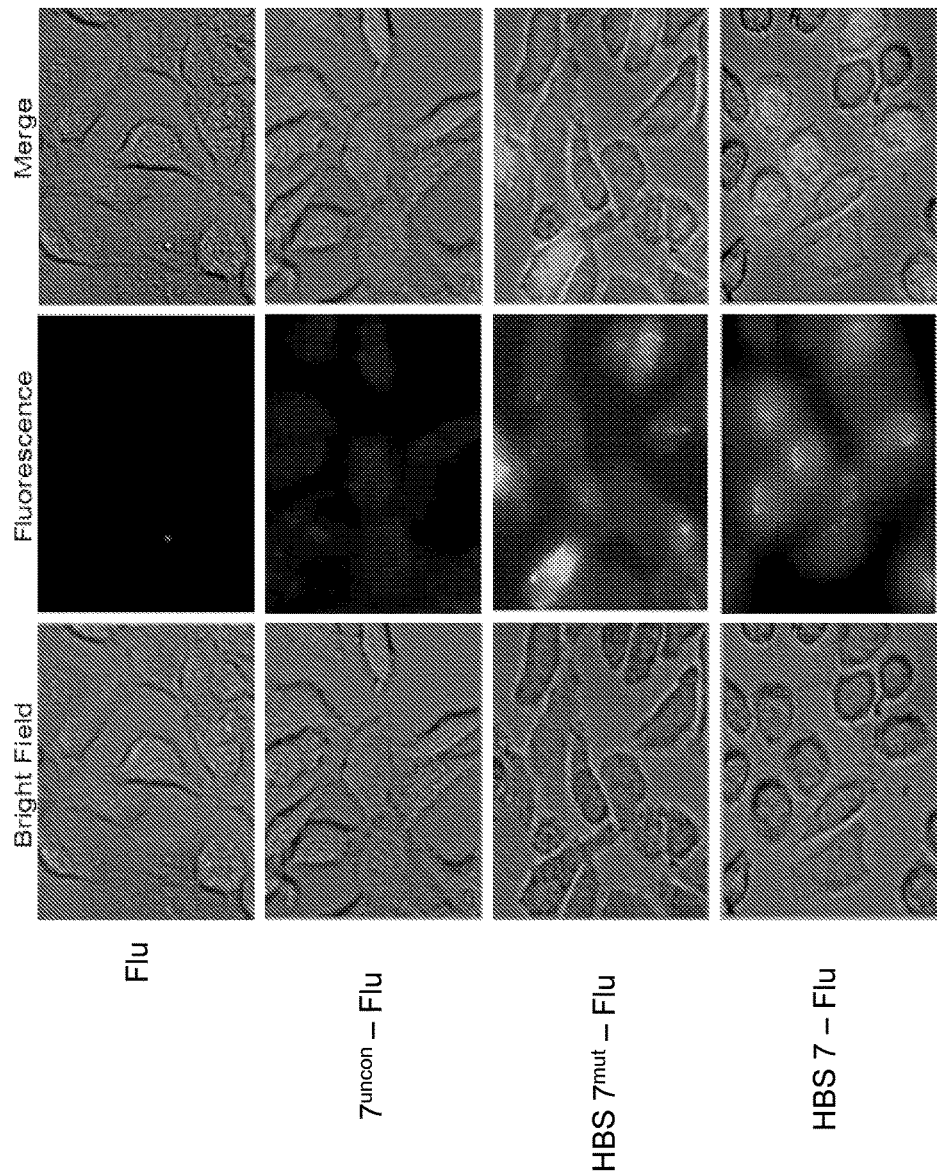
FIG. 11 shows cellular uptake of HBS peptides into live HeLa cells.
Figure 12:
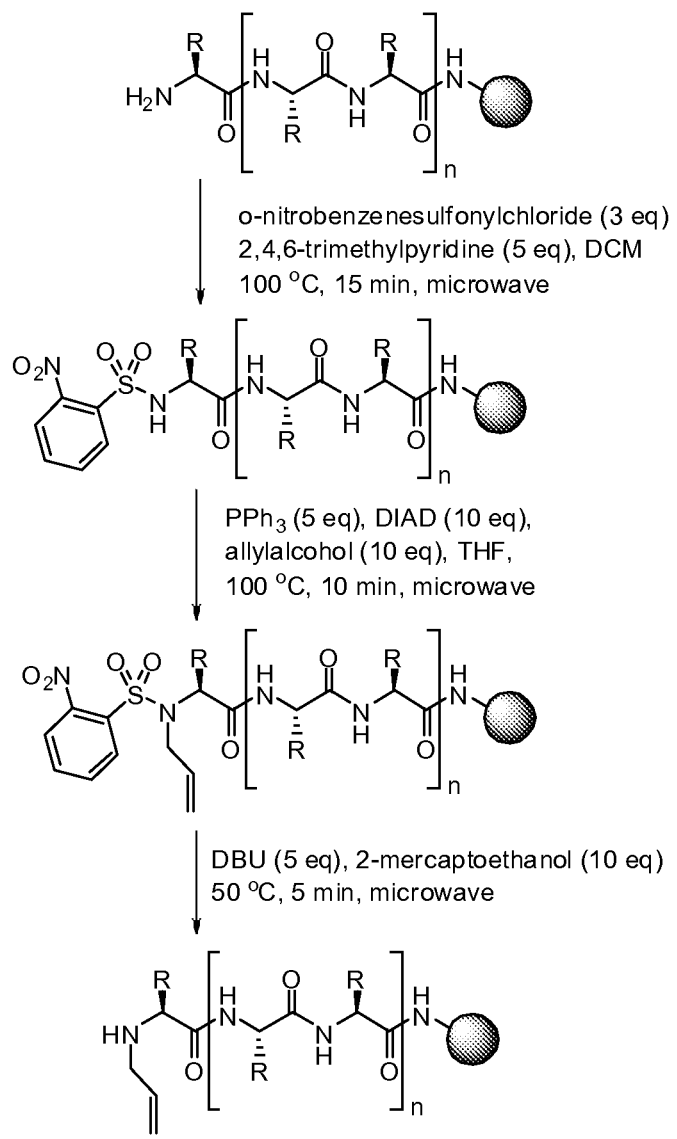
FIG. 12 shows a synthetic scheme for preparation of HBS 13 and related compounds.
Figure 13:
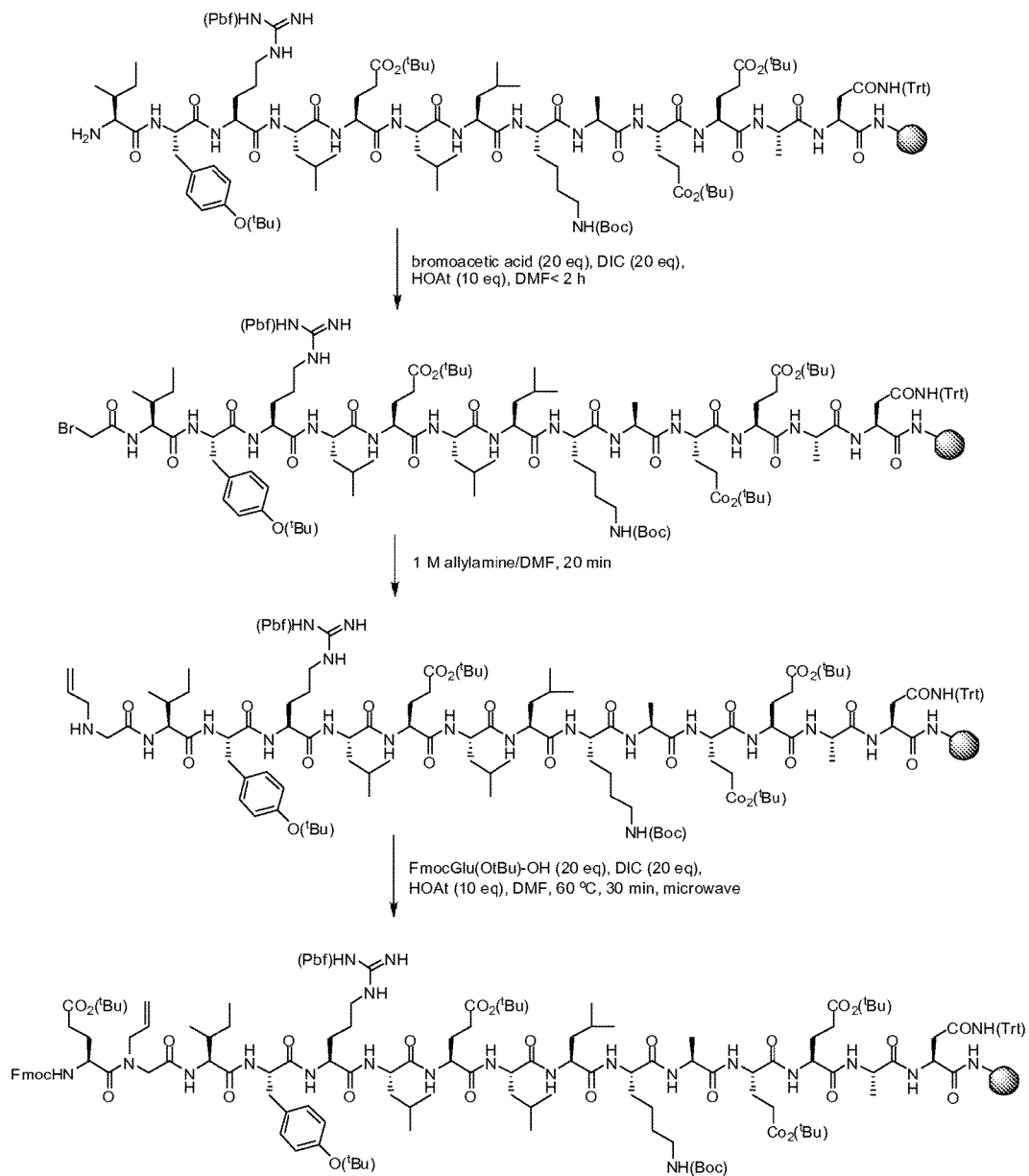
FIG. 13 shows a synthetic scheme for preparation of HBS 7 and related compounds.
Figure 14:
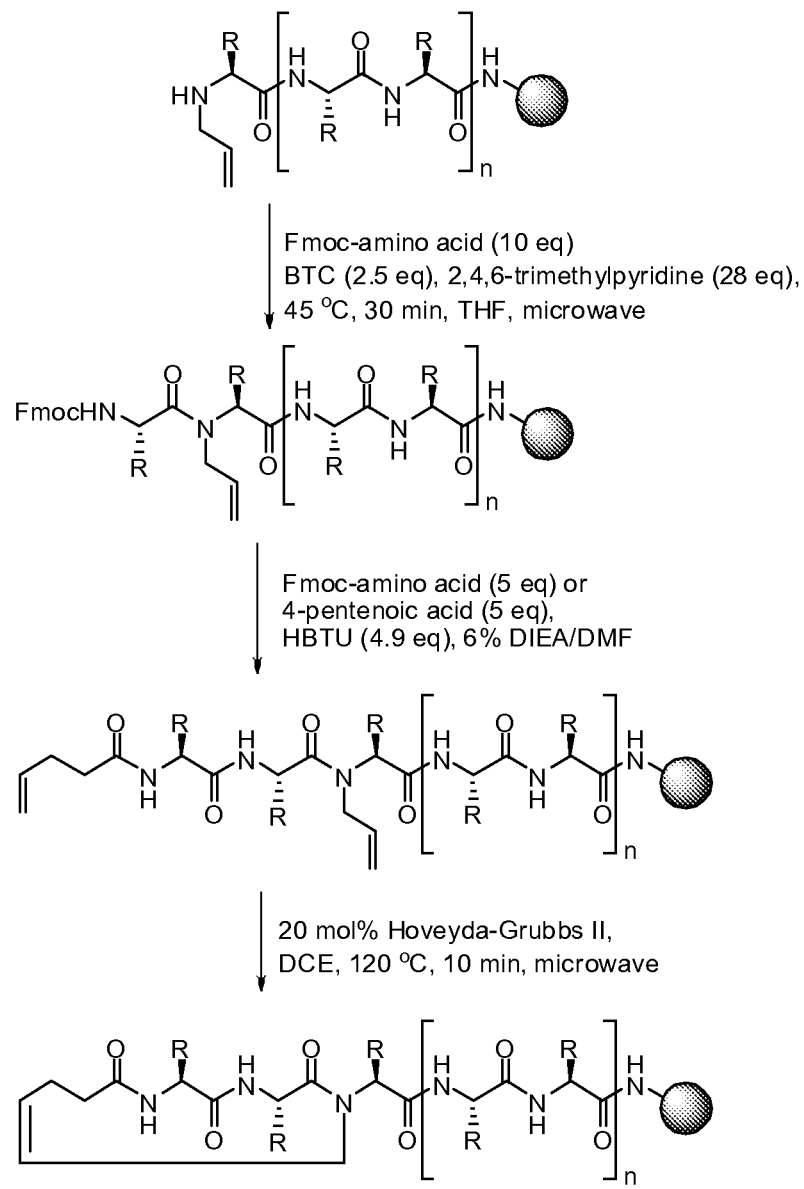
FIG. 14 shows a synthetic scheme for preparation of various HBS peptides of the invention.
Figure 15:
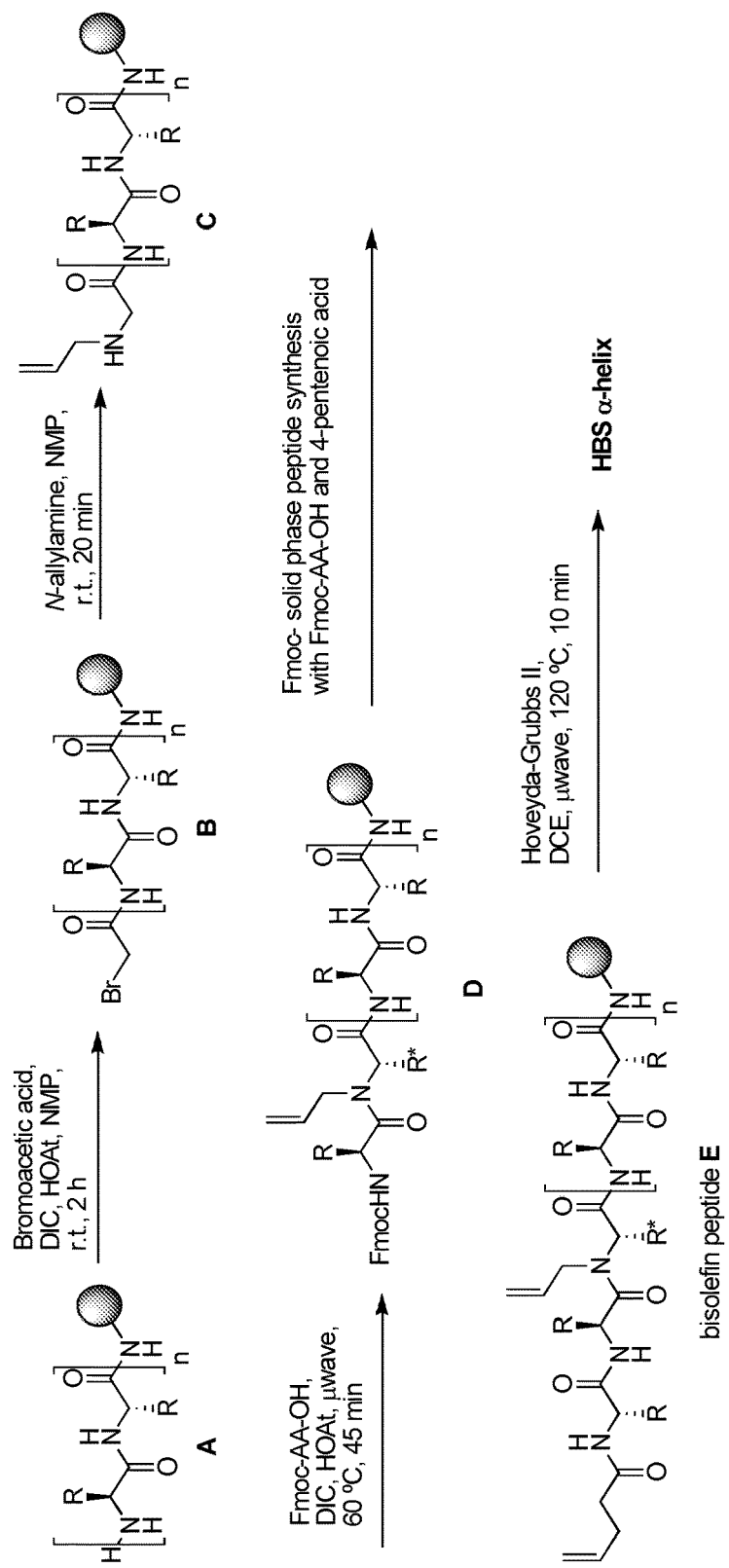
FIG. 15 shows a synthetic scheme for the preparation of HBS peptides containing a glycine residue at the third position from the N-terminus.

Example 3—Affinity of Peptides for Ras Protein as Determined by Fluorescence Polarization The relative affinity of peptides for N-terminal His$_6$-tagged Ras$_{1-166}$ was determined using fluorescence polarization based binding assay with fluorescein labeled SOS peptides 7$^{uncon}$-Flu, HBS 7-Flu and HBS 7$^{mut}$-Flu. The polarization experiments were performed with a DTX 880 Multimode Detector (Beckman) at 25° C., with excitation and emission wavelengths at 485 and 525 nm, respectively. All samples were prepared in 96 well plates in 0.1% pluronic F-68 (Sigma). Addition of an increasing concentration (0 nm to 750 µM) of Ras$_{1-166}$ protein to a 15 nM solution of fluorescein labeled SOS peptide in Ras$_{1-166}$ dialysis buffer afforded the saturation binding curve. The IC$_{50}$ value obtained from this binding curve was fit into equation (1) to calculate the dissociation constant (K$_D$) for the Sos/Ras$_{1-166}$ complex. The binding affinity (K$_D$) values reported for each peptide are the averages of 3 individual experiments, and were determined by fitting the experimental data to a sigmoidal dose-response nonlinear regression model on Graph-Pad Prism 4.0. Results are shown in FIG. 10.

$$K_{D1}=(R_T*(1-F_{SB})+L_{ST}*F_{SB}^2)/F_{SB}-L_{ST} \qquad (1)$$

where:
$R_T$=Total concentration of Ras$_{1-166}$ protein
$L_{ST}$=Total concentration of Sos fluorescent peptide
$F_{SB}$=Fraction of bound Sos fluorescent peptide

Figure 4:
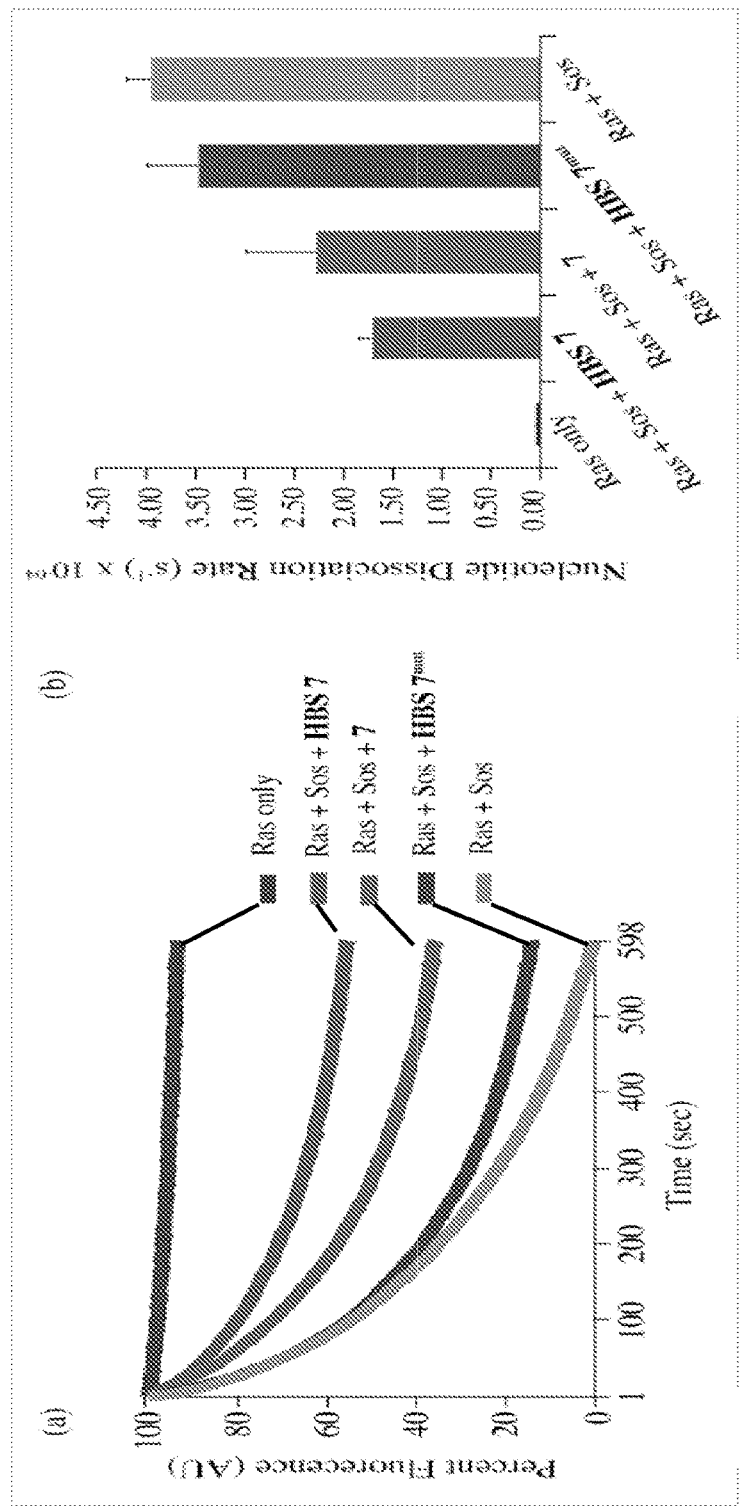
FIG. 4 shows inhibition of Sos-mediated guanine nucleotide exchange activity by compositions of the invention.

Example 4—Assay for Inhibition of Sos-Mediated Guanine Nucleotide Exchange Activity by Peptides of the Invention Nucleotide exchange assays using mantGDP were performed as described by Ahmadian et al., 2002; and Margarit et al., 2003. Briefly, purified Ras (residues 1-166 of human Ha-Ras) was incubated in an equimolar amount of mantGDP in the presence of 4 mM EDTA in exchange buffer (20 mM Tris [pH 7.4], 50 mM NaCl). Reactions were stopped with 14 mM MgCl$_2$. Nucleotide dissociation rates were measured by incubation of 1 µM Ras•mantGDP in reaction buffer (20 mM Tris [pH 7.4], 14 mM MgCl2, and 50 mM NaCl) supplemented with 25 µM peptides, 5 µM Sos-Cat and 100 µM unlabeled GDP. The data were fitted to a single exponential decay function using the program Prism (GraphPad Software Inc.). Results are shown in FIG. 4.

Example 5—GST Assays for Inhibition of Ras/Sos by Peptides of the Invention

Figure 6:
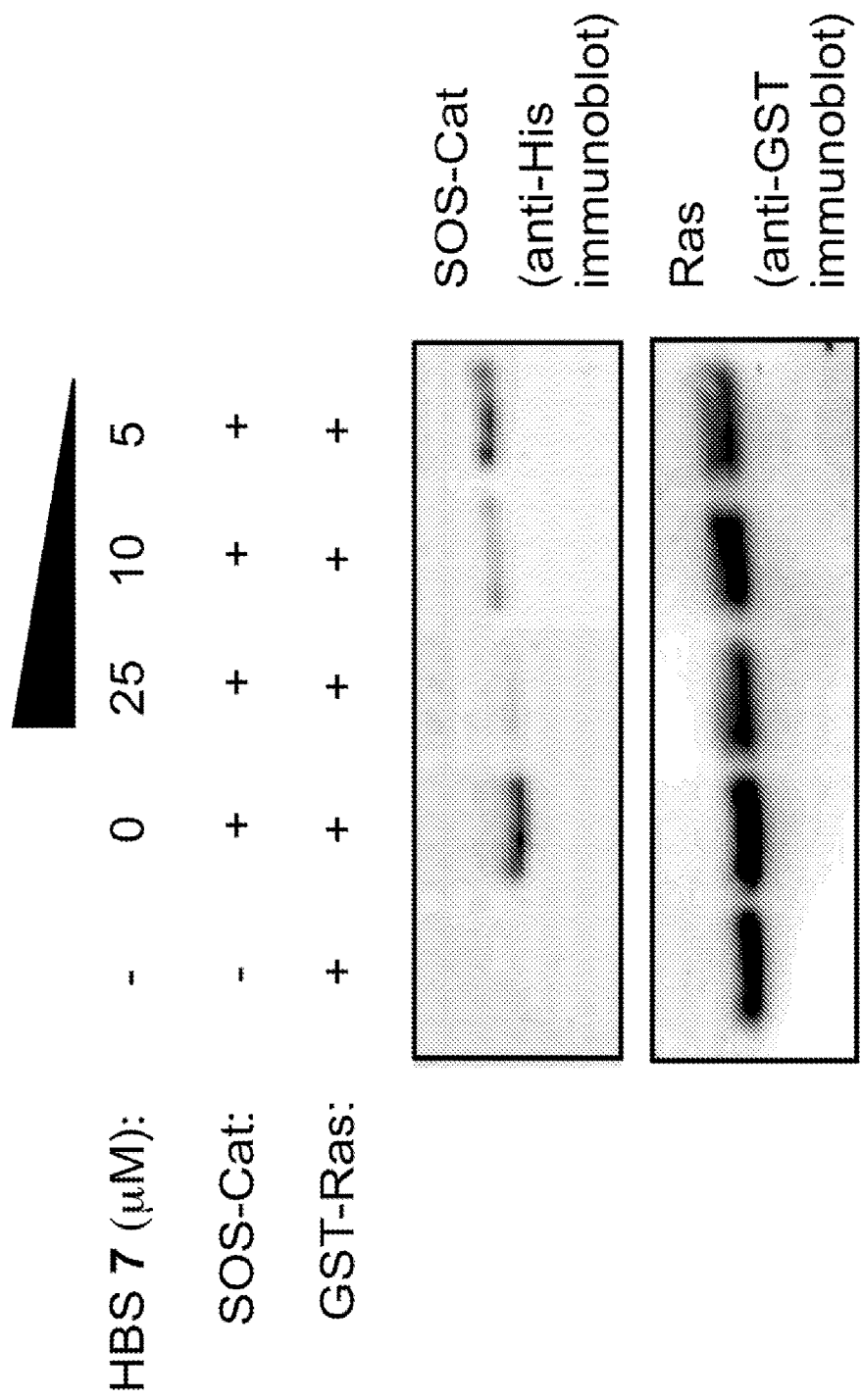
FIG. 6 shows inhibition of the Ras/Sos complex by HBS 7 as evaluated in a GST pull-down assay in the presence of 40 nM Sos and 100 nM GST-Ras.
Figure 7:
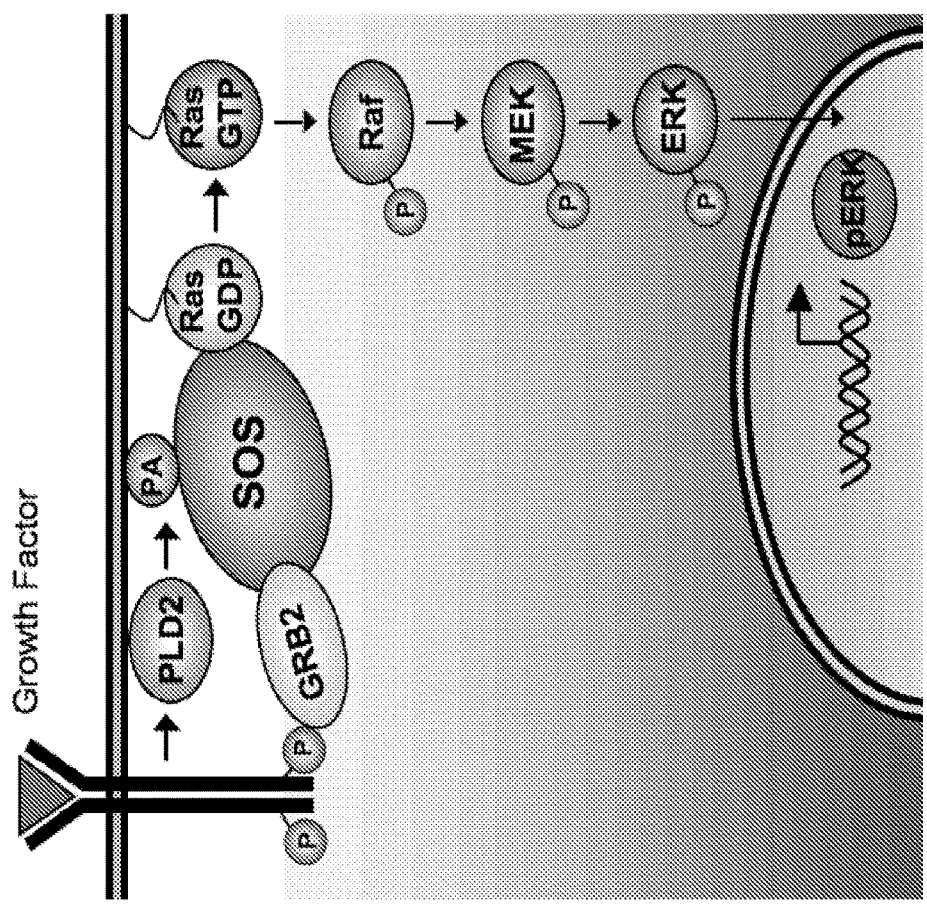
FIG. 7 shows a schematic of the RTK/Ras/MAPK signaling network leading to gene expression.

GST-Ras fusion protein (1 µM), His-tagged Sos protein (1 µM) and the indicated amount of HBS 7 were added to 1 ml of binding buffer (20 mM Tris (pH 7.6), 50 mM NaCl, 1 mM dithiothreitol, 5 mM EDTA, and 1% Triton X-100) and incubated at 4° C. for 30 min. Following incubation, 60 µl of 1:1 slurry of glutathione-Sepharose 4B beads resuspended in binding buffer were added to each sample. Samples were incubated for an additional 20 min at 4° C. Beads were subsequently pelleted, washed five times with binding buffer, and resuspended in SDS-polyacrylamide gel electrophoresis sample buffer. Proteins were separated by SDS-polyacrylamide gel electrophoresis and transferred to nitrocellulose. Western blots were probed with anti-His antibody and anti-GST antibody to detect Sos and Ras, respectively, and the results are shown in FIG. 6.

Example 6—Ras Activation Assays

Figure 8:
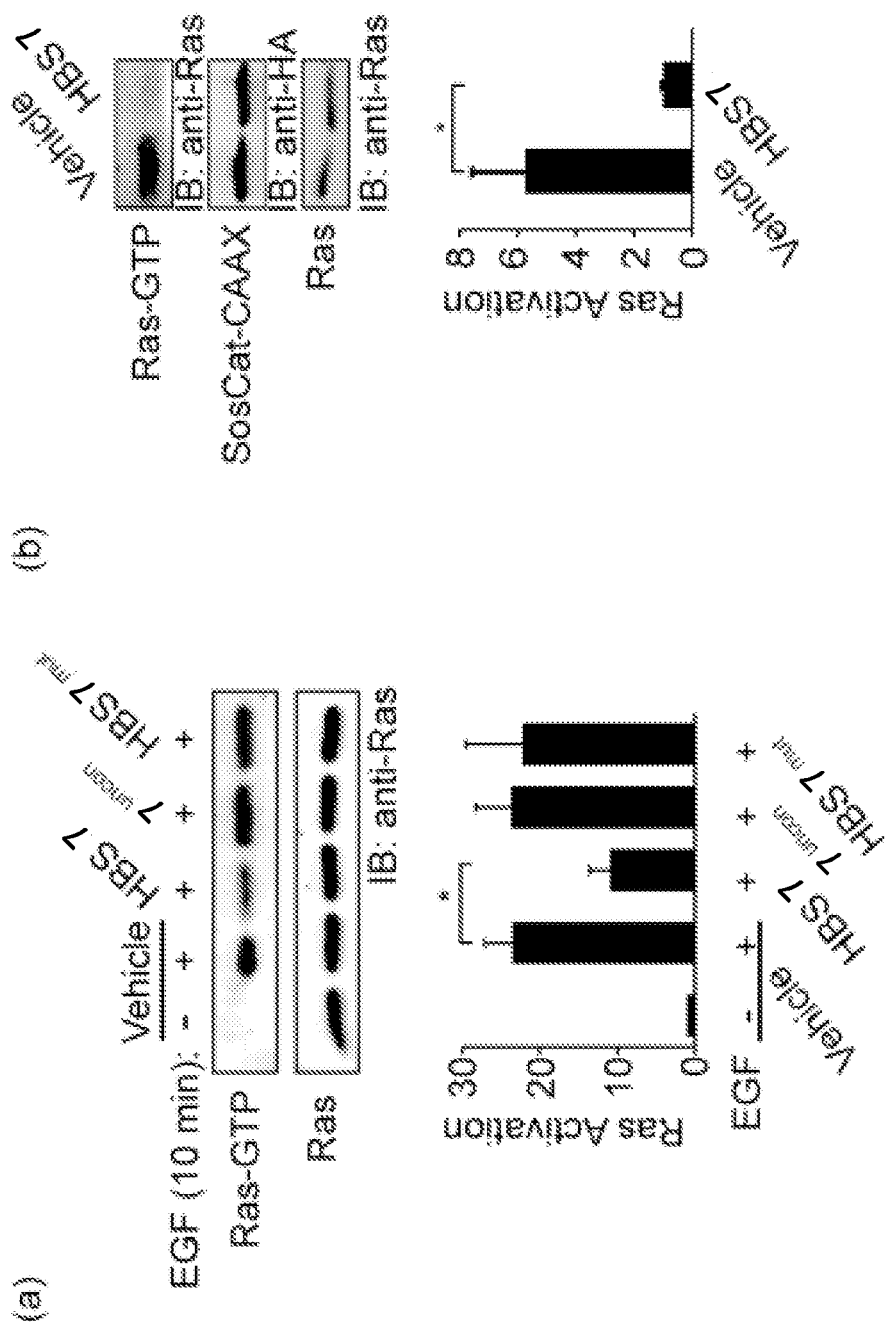
FIGS. 8a-d show the effect of FIBS peptides of the invention upon RTK/Ras pathway proteins as determined by experiments on cell cultures.
Figure 8:
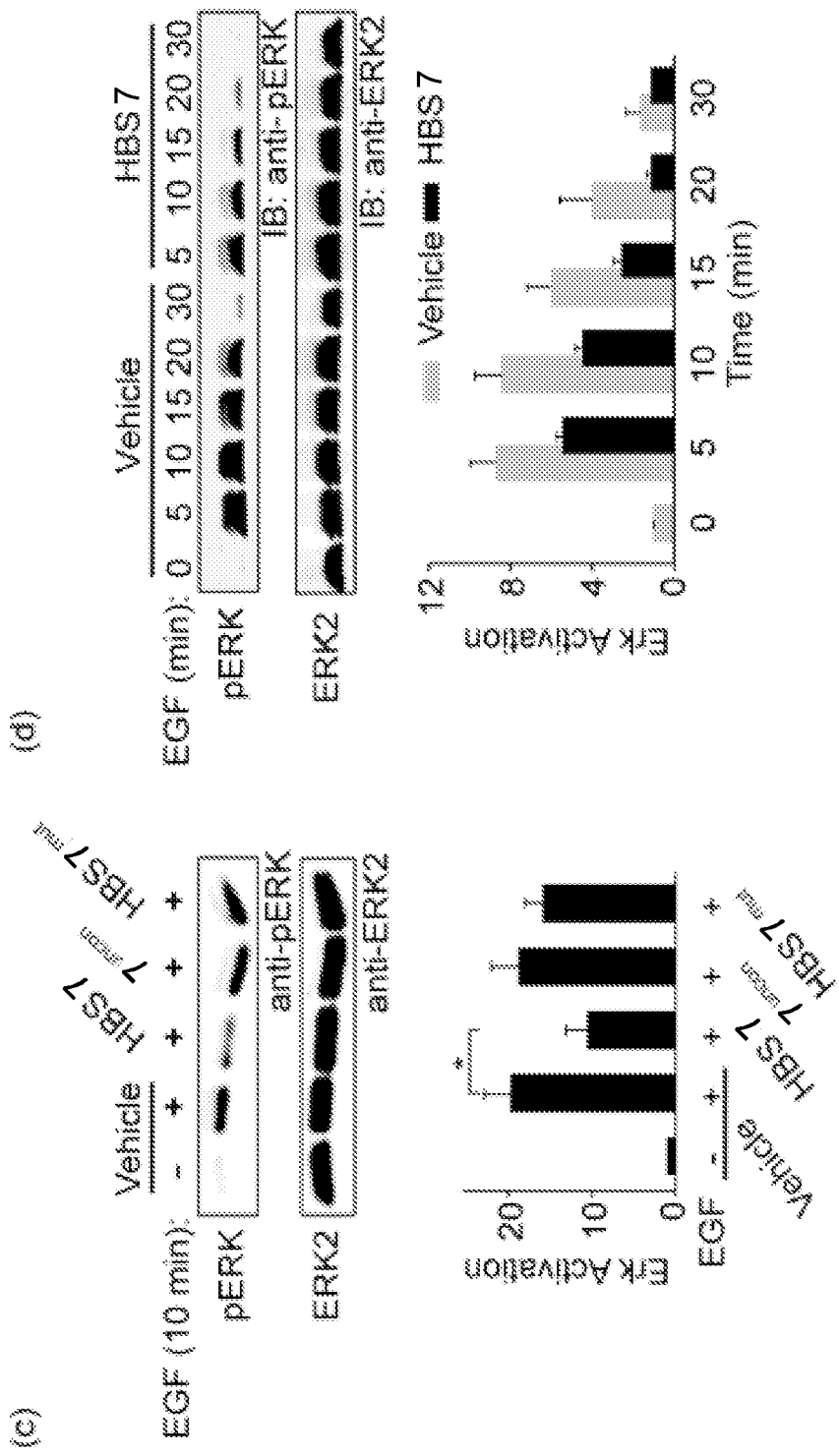

The RBD-pull down assay was carried out as described in Boykevisch S, Zhao C, Sondermann H, Philippidou P, Halegoua S, Kuriyan J, Bar-Sagi D. Regulation of ras signaling dynamics by Sos-mediated positive feedback Curr Biol. 2006 Nov. 7; 16(21):2173-9 and as described herein. GST-Raf-RBD fusion proteins were expressed in *E. coli* by induction with 0.5 mM of isopropyl-1-thio-β-D-galactopyranoside (IPTG) for 5 hours. The expressed fusion proteins were isolated from bacteria lysates by incubation with glutathione agarose beads for 1 hour at 4° C. HeLa cells were grown to confluence, serum-starved for 4 hours, and incubated with 75 µM peptide for an additional 12 hours. For experiments with SosCat-CAAX (SosCat with CAAX box of HRas), HeLa cells were transfected with HA-tagged SosCAAX twenty four hours prior to starvation. Cells were treated with the indicated peptides for 12 hours prior to stimulation. After stimulation with 10 ng/ml EGF for the indicated intervals at 37° C., the cells were lysed in RBD lysis buffer containing 25 mM Tris-HCl (pH 7.4), 120 mM NaCl, 10 mM MgCl2, 1 mM EDTA, 10% glycerol, 10 mg/ml pepstatin, 50 mM NaF, 1% aprotinin, 10 mg/ml leupeptin, 1 mM Na3VO4, 10 mM benzamidine, 10 mg/ml soybean trypsin inhibitor, 1% NP40, and 0.25% sodium deoxycholic acid. The lysates were then incubated with 20 µg of recombinant GST-Raf-RBD immobilized to agarose beads for 1.5 hours at 4° C. The complexes were collected by centrifugation and washed six times with the RBD lysis buffer. Bound proteins were eluted with SDS sample buffer, separated by SDS-12.5% PAGE and transferred to nitrocellulose membrane. The proteins were detected by blotting with anti-HA (12CA5; 1:10,000) for SosCatCAAX or anti-Ras10 (Millipore; 1:10,000) primary antibodies and Alexa Fluor 680 goat anti-mouse (Molecular Probes, 1:10,000) secondary antibody and visualized with the Odyssey infrared imaging System (LiCor). Results are shown in FIG. 8.

Example 7—EGFR and Erk Activation Assays

Mitogen-activated protein kinase (MAPK) signal transduction pathways are widespread mechanisms of eukaryotic cell regulation (FIG. 6). MAPK is involved in control of activities including cellular metabolism, motility, survival, apoptosis, and differentiation. Ras activation by Sos is closely tied to the initiation of this signaling pathway, which ultimately leads to expression of a variety of genes including those controlled by the serum response element within the IEG (immediately early gene) promoter. Peptides were tested in an assay to determine their ability to inhibit Erk and/or EGFR activation. Cells were treated and lysed as described above, and as described in Boykevisch S, Zhao C, Sondermann H, Philippidou P, Halegoua S, Kuriyan J, Bar-Sagi D. Regulation of ras signaling dynamics by Sos-mediated positive feedback Curr Biol. 2006 Nov. 7; 16(21): 2173-9, and Xu L, Lubkov V, Taylor L J, Bar-Sagi D. Feedback regulation of Ras signaling by Rabex-5-mediated ubiquitination. Curr Biol. 2010 Aug. 10; 20(15):1372-7, which are hereby incorporated by reference in their entirety. Levels of total ERK2 and phosphorylated ERK were detected with anti-ERK2 (Upstate Biotechnology, 1:1,000) and phospho-ERK1/2 (Cell Signaling, 1:1,000) antibodies, respectively. ERK phosphorylation levels were quantified with the Odyssey software and normalized to total ERK expression. EGFR and pEGFR levels were detected by blotting with anti-EGFR (Santa Cruz Biotech) and pEGFR pY1068 (Cell Signaling) antibodies. Results are shown in FIG. 8.

Example 8—Cellular Uptake Assays

HeLa cells were plated at sub-confluency in DMEM supplemented with 10% FBS in a 96 well plate with glass bottom. The following day, media was replaced with one supplemented with 1 µM fluorescein (5-FAM) only or fluorescein-tagged peptides as indicated. After 12 hours, the cells were washed twice with warm PBS and imaged directly with the Zeiss Axiovert 200M microscope.

Example 9—NMR Experiments

His6-Ras (1-166) and Sos-Cat (564-1049) Expression. His6-tagged HRas (residues 1-166) and His6-tagged SosCat (residues 550-1050) both in pProEx HTb expression vectors, were expressed in *Escherichia coli* (BL21) by induction with 500 µM IPTG at a cell density corresponding to an absorbance of OD600=1.0. Pellets were resuspended in buffer containing 20 mM Tris pH7.6, 200 mM NaCl, 2.5 mM MgCl2, 2 µM phenylmethylsulfonylfluride (PMSF), 1% aprotinin, 10 µg/ml leupeptin, 10 mM benzamidine, 10 µg/ml soybean trypsin inhibitor, and 10 µg/ml pepstatin, and sonicated using a Branson Cell Disrupter 200. Clarified lysates containing polyhistidine tagged proteins were incubated with charged nickel resin (Invitrogen) at 4° C. for 1 hour. The resin was washed five times in resuspension buffer containing 50 mM imidazole. The tagged proteins were eluded with buffer containing 200 mM imidazole in 20 mM Tris pH 7.6, 200 mM NaCl. Eluted proteins were dialyzed against buffer containing 20 mM Tris pH 7.6 and 200 mM NaCl for His-tagged SosCat, and 20 mM Tris pH 7.6, 200 mM NaCl and 1 mM MgCl2 for His-tagged Ras. The eluted proteins were concentrated with 5,000 kD molecular cut-off Amicon ultra centrifugal columns (Millipore). Purified proteins were snap frozen in liquid N2 and stored at −80° C. till further use.

Figure 5A:
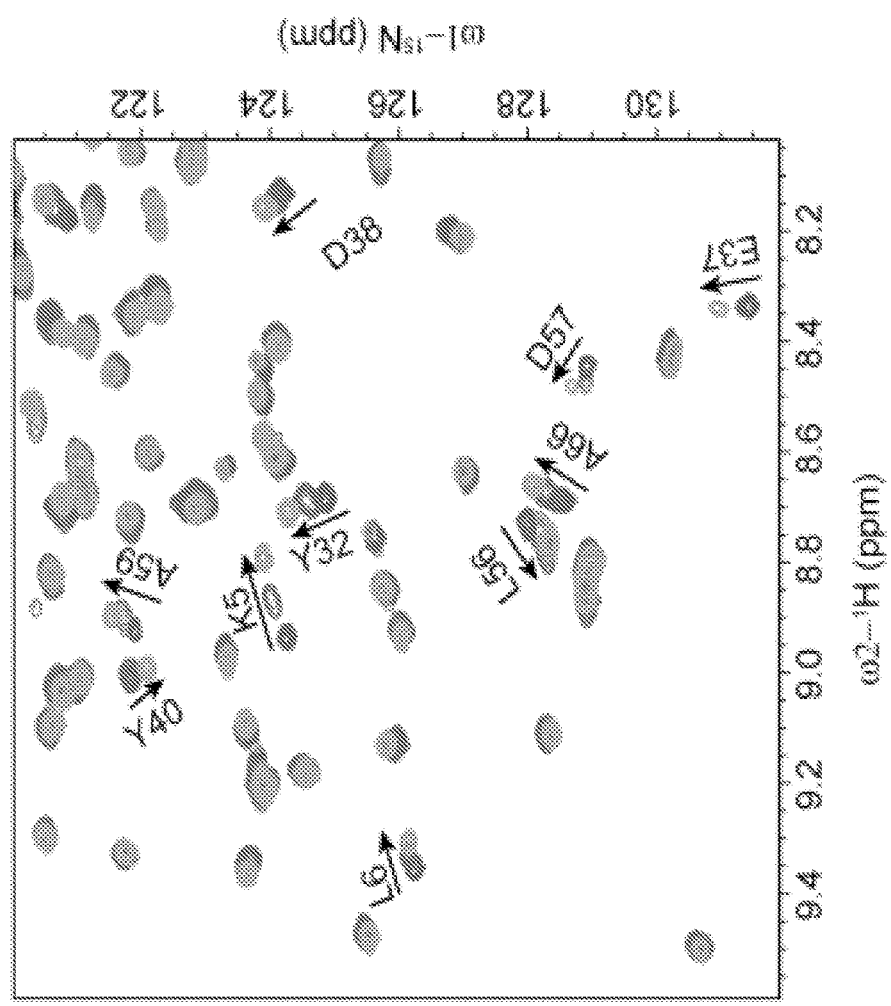
FIG. 5A shows selected changes in $^1$H-$^{15}$N HSQC spectra of $^{15}$N-labelled Ras resonances upon addition of three and five equivalents of HBS 7.
Figure 5B:
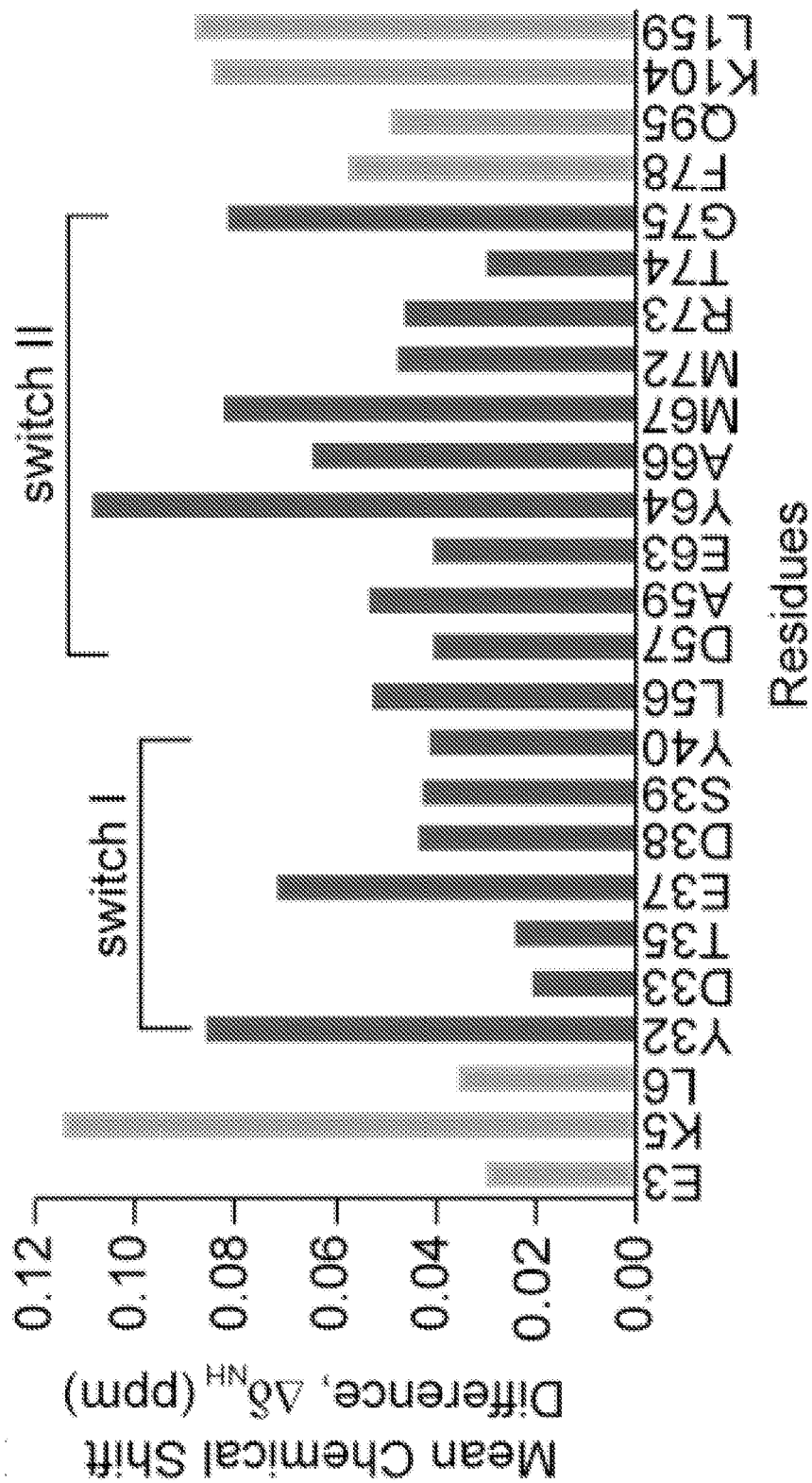
FIG. 5B shows a plot of mean chemical shift differences illustrating changes upon the addition of increasing amounts of HBS 7.

For $^1$H-$^{15}$N HSQC NMR experiments, BL21 cells harbouring the His-Ras construct were grown at 37° C. in M9 media supplemented with $^{15}$NH$_4$Cl as the sole source of nitrogen[15]. Protein production was induced with 500 µM IPTG at O.D. 1.0 for 16 hours at 16° C. Protein purification and concentration were performed as in Section 5. The His$_6$-tag was removed by incubating the His6-tagged Ras with recombinant His6-tagged Tobacco Etch Virus (TEV) protease (Invitrogen) overnight at 4° C. following manufacturer's protocol. The sample was loaded on a charged NiNTA agarose column and the tag-less protein collected in the flow through fraction. Uniformly $^{15}$N-labelled Ras was buffer exchanged against the NMR buffer (20 mM Na2HPO4-NaH2PO4, pH 5.5, 150 mM NaCl, 10 mM MgCl2) using Amicon Ultra centrifugal filter (Millipore) and supplemented with 10% D$_2$O. Data was collected on a 900 MHz Bruker four-channel NMR system equipped with cryoprobe at 30° C. and analyzed with the BioSpin software (Bruker). Mean chemical shift difference (ΔδNH) observed for $^1$H and $^{15}$N nuclei of various resonances corresponding to residues in the switch and non-switch regions were calculated. Results of an NMR experiments are shown in FIG. 5.

Example 10—Peptide Design

Design of Ras/Sos inhibitors was performed starting with the wild-type Sos$_{929-944}$ α-H sequence. Additional modifications were introduced in order to improve the solubility of the HBS peptides. Charged residues were introduced at positions not involved in Ras binding. Computational alanine scanning was performed on two separate crystal structures (PDB codes: 1NVW and 1BKD) of the Ras/Sos complex to determine other important binding residues in the α-H helix that may be incorporated in the peptide mimetics. Additionally, non-essential β-branched residues (including threonine) in the wild-type α-H sequence were replaced with suitable residues to afford peptides with higher helical content (Table 1), as it was hypothesized that such modifications would improve α-helicity.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A peptide having a stable, internally-constrained alpha-helix, wherein said alpha helix is constrained by a crosslink formed by a carbon-carbon bond-forming reaction, and further wherein the peptide mimics at least an alpha helical portion of a protein capable of interacting with a Ras protein, wherein the peptide comprises the sequence of formula FXGZZXZXZLXZEXXN (SEQ ID NO: 1) where X is any amino acid residue and Z is a hydrophobic residue.

2. The peptide of claim 1, wherein the protein capable of interacting with a Ras protein is Sos.

3. The peptide of claim 2, wherein the peptide mimics at least a portion of an αA, αB, αC, αD, αE, αF, αG, αH, αI, αJ, or αK helix of Sos.

4. The peptide of claim 3, wherein the peptide mimics at least a portion of the αH helix of Sos.

5. The peptide of claim 4, wherein the peptide mimics amino acids 929-944 of the αH sequence of Sos.

6. The peptide of claim 1, wherein the peptide comprises:
   (i) the sequence X'FEGIYRTDILRTEEGN,
   (ii) the sequence X'FEGIYRTELLKAEEAN,
   (iii) the sequence X'FEGLLRLWLRKXEEAN where X is α-aminoisobutyric acid,
   (iv) the sequence X'FEGLLRLWLRKXEEXN where X is α-aminoisobutyric acid,
   (v) the sequence X'FEGIYRLELLKXEEXN where X is α-aminoisobutyric acid,
   (vi) the sequence X'FEGLLRLWLRKAEEAN,
   (vii) the sequence X'FEAIYRLEKLKAEEAN, or
   (viii) the sequence X'FEGIYRLEKLKAEEANRR,
   wherein X' is a 4-pentenoyl group, and
   wherein the peptide has an internally-constrained alpha-helix spanning residues 1 through 4 of the amino acid sequence.

7. The peptide of claim 1, wherein the peptide comprises the formula:

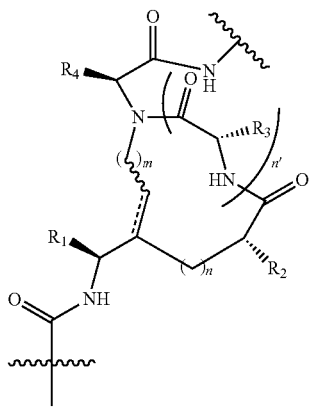

where
⸺ is a single or double carbon-carbon bond;
∿∿ is a single bond and is cis or trans when ⸺ is a double bond;
n and n' are each independently 1 or 2;
m is zero or any positive integer; and
$R_1$, $R_2$, each $R_3$, and $R_4$ are independently hydrogen, an amino acid side chain, an alkyl group, or an aryl group.

8. The peptide of claim 7, wherein n' is 2 and m is 1.

9. The peptide of claim 7, wherein n' is 2 and n is 1.

10. A pharmaceutical composition comprising a peptide according to claim 1 and a pharmaceutically acceptable vehicle.

11. The peptide of claim 1, wherein the peptide does not comprise the sequence FEGIYRLELLKAEEAN (SEQ ID NO: 9) or FEAIYRLELLKAEEAN (SEQ ID NO: 16).

12. The peptide of claim 11 wherein the peptide comprises the formula:

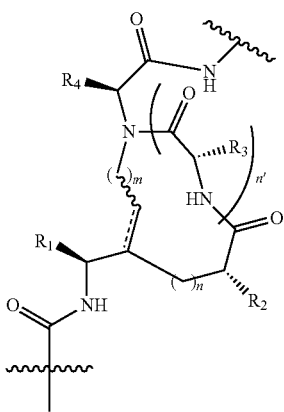

where
------ is a single or double carbon-carbon bond;
⌇⌇⌇ is a single bond and is cis or trans when ------ is a double bond;
n and n' are each independently 1 or 2;
m is zero or any positive integer; and
$R_1$, $R_2$, each $R_3$, and $R_4$ are independently hydrogen, an amino acid side chain, an alkyl group, or an aryl group.

13. The peptide of claim 12, wherein n' is 2 and m is 1.

14. The peptide of claim 12, wherein n' is 2 and n is 1.

15. The peptide of claim 1, wherein the peptide comprises the formula:

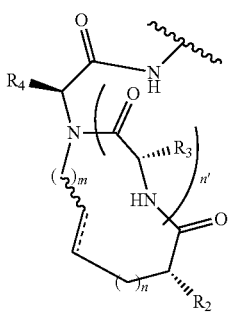

where
------ is a single or double carbon-carbon bond;
⌇⌇⌇ is a single bond and is cis or trans when ------ is a double bond;
n and n' are each independently 1 or 2;
m is zero or any positive integer; and
$R_1$, $R_2$, each $R_3$, and $R_4$ are independently hydrogen, an amino acid side chain, an alkyl group, or an aryl group.

16. The peptide of claim 15, wherein n' is 2 and m is 1.

17. The peptide of claim 15, wherein n' is 2 and n is 1.

18. The peptide of claim 11, wherein the peptide comprises the formula:

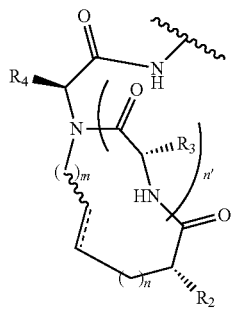

where
------ is a single or double carbon-carbon bond;
⌇⌇⌇ is a single bond and is cis or trans when ------ is a double bond;
n and n' are each independently 1 or 2;
m is zero or any positive integer; and
$R_1$, $R_2$, each $R_3$, and $R_4$ are independently hydrogen, an amino acid side chain, an alkyl group, or an aryl group.

19. The peptide of claim 18, wherein n' is 2 and m is 1.

20. The peptide of claim 18, wherein n' is 2 and n is 1.

21. A peptide having a stable, internally-constrained alpha-helix, wherein said alpha helix is constrained by a crosslink formed by a carbon-carbon bond-forming reaction, and further wherein the peptide mimics at least an alpha helical portion of a protein capable of interacting with a Ras protein, wherein the peptide comprises the formula:

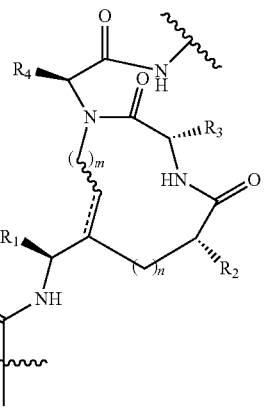

or

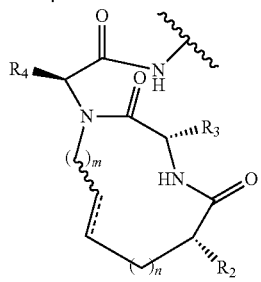

where
------ is a single or double carbon-carbon bond;
⌇⌇⌇ is a single bond and is cis or trans when ------ is a double bond;
n is 1;
n' is 2;
m is 1; and R₁, R₂, each R₃, and R₄ are independently hydrogen, an amino acid side chain, an alkyl group, or an aryl group.

22. The peptide of claim 21, wherein the protein capable of interacting with a Ras protein is Sos.

23. The peptide of claim 22, wherein the peptide mimics at least a portion of an αA, αB, αC, αD, αF, αF, αG, αH, αI, αJ, or αK helix of Sos.

24. The peptide of claim 23, wherein the peptide mimics at least a portion of the αH helix of Sos.

25. The peptide of claim 24, wherein the peptide mimics amino acids 929-944 of the αH sequence of Sos.

26. The peptide of claim 21, wherein the peptide comprises:
(i) the sequence X'FEGIYRTDILRTEEGN,
(ii) the sequence X'FEGIYRTELLKAEEAN,
(iii) the sequence X'FEGLLRLWLRKXEEAN where X is α-aminoisobutyric acid,
(iv) the sequence X'FEGLLRLWLRKXEEXN where X is α-aminoisobutyric acid,
(v) the sequence X'FEGIYRLELLKXEEXN where X is α-aminoisobutyric acid,
(vi) the sequence X'FEGLLRLWLRKAEEAN,
(vii) the sequence X'FEAIYRLEKLKAEEAN, or
(viii) the sequence X'FEGIYRLEKLKAEEANRR,
wherein X' is a 4-pentenoyl group, and
wherein the peptide has an internally-constrained alpha-helix spanning residues 1 through 4 of the amino acid sequence.

27. The peptide of claim 21, wherein the peptide comprises the formula:

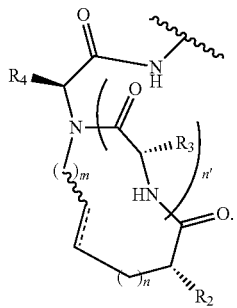

28. The peptide of claim 21, wherein the peptide comprises the formula:

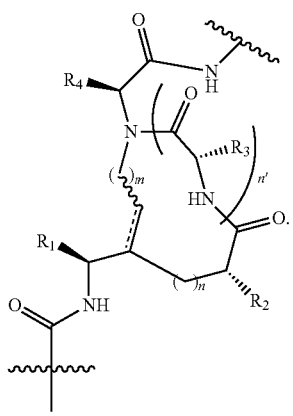

29. The peptide of claim 21, wherein the peptide does not comprise the sequence FEGIYRLELLKAEEAN (SEQ ID NO: 9) or FEAIYRLELLKAEEAN (SEQ ID NO: 16).

30. A pharmaceutical composition comprising a peptide according to claim 21 and a pharmaceutically acceptable vehicle.

31. The peptide of claim 7, wherein n' is 2 and m is 2.

32. The peptide of claim 7, wherein n' is 2 and n is 2.

33. A method of inhibiting Ras signaling in a cell, comprising contacting the cell with an effective amount of a composition comprising a peptide according to claim 1.

34. The method of claim 33, wherein the protein capable of interacting with a Ras protein is Sos.

35. The method of claim 34, wherein the peptide mimics at least a portion of an αA, αB, αC, αD, αE, αF, αG, αH, αI, αJ, or αK helix of Sos.

36. The method of claim 35, wherein the peptide mimics at least a portion of the αH helix of Sos.

37. The method of claim 36, wherein the peptide mimics amino acids 929-944 of the αH sequence of Sos.

38. The method of claim 33, wherein the peptide comprises:
(i) the sequence X'FEGIYRTDILRTEEGN,
(ii) the sequence X'FEGIYRTELLKAEEAN,
(iii) the sequence X'FEGLLRLWLRKXEEAN where X is α-aminoisobutyric acid,
(iv) the sequence X'FEGLLRLWLRKXEEXN where X is α-aminoisobutyric acid,
(v) the sequence X'FEGIYRLELLKXEEXN where X is α-aminoisobutyric acid,
(vi) the sequence X'FEGLLRLWLRKAEEAN,
(vii) the sequence X'FEAIYRLEKLKAEEAN, or
(viii) the sequence X'FEGIYRLEKLKAEEANRR,
wherein X' is a 4-pentenoyl group, and
wherein the peptide has an internally-constrained alpha-helix spanning residues 1 through 4 of the amino acid sequence.

39. The method of claim 33, wherein the peptide comprises the formula:

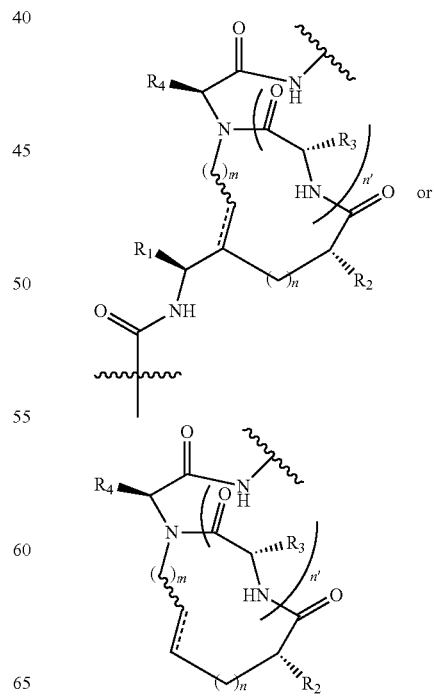

where
 is a single or double carbon-carbon bond;
 is a single bond and is cis or trans when  is a double bond;
n and n' are each independently 1 or 2;
m is zero or any positive integer; and
$R_1$, $R_2$, each $R_3$, and $R_4$ are independently hydrogen, an amino acid side chain, an alkyl group, or an aryl group.

40. The method of claim 39, wherein n' is 2 and m is 1.
41. The method of claim 39, wherein n' is 2 and m is 2.
42. The method of claim 39, wherein n' is 2 and n is 1.
43. The method of claim 39, wherein n' is 2 and n is 2.
44. A method of treating cancer in a subject in need thereof, comprising administering to the subject a peptide according to claim 1.
45. The method of claim 44, wherein the peptide comprises:
(i) the sequence X'FEGIYRTDILRTEEGN,
(ii) the sequence X'FEGIYRTELLKAEEAN,
(iii) the sequence X'FEGLLRLWLRKXEEAN where X is α-aminoisobutyric acid,
(iv) the sequence X'FEGLLRLWLRKXEEXN where X is α-aminoisobutyric acid,
(v) the sequence X'FEGIYRLELLKXEEXN where X is α-aminoisobutyric acid,
(vi) the sequence X'FEGLLRLWLRKAEEAN,
(vii) the sequence X'FEAIYRLEKLKAEEAN, or
(viii) the sequence X'FEGIYRLEKLKAEEANRR,
wherein X' is a 4-pentenoyl group, and
wherein the peptide has an internally-constrained alpha-helix spanning residues 1 through 4 of the amino acid sequence.
46. The method of claim 44, wherein the peptide comprises the formula:

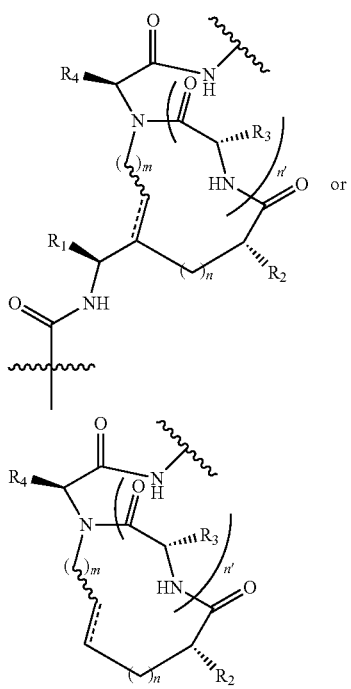

where
 is a single or double carbon-carbon bond;
 is a single bond and is cis or trans when  is a double bond;
n and n' are each independently 1 or 2;
m is zero or any positive integer; and
$R_1$, $R_2$, each $R_3$, and $R_4$ are independently hydrogen, an amino acid side chain, an alkyl group, or an aryl group.

47. The peptide of claim 12, wherein n' is 2 and m is 2.
48. The peptide of claim 12, wherein n' is 2 and n is 2.
49. The method of claim 33, wherein the peptide does not comprise the sequence FEGIYRLELLKAEEAN (SEQ ID NO: 9) or FEAIYRLELLKAEEAN (SEQ ID NO: 16).
50. The method of claim 49, wherein the peptide comprises the formula:

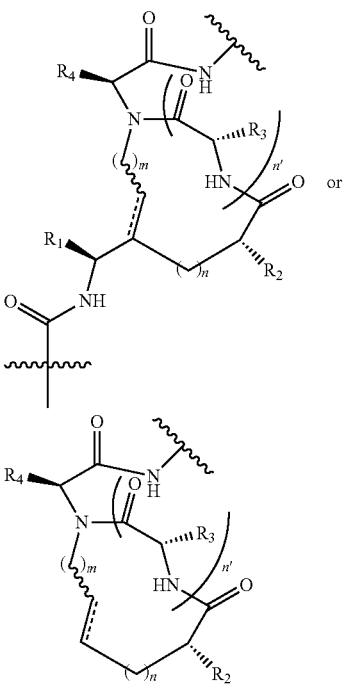

where
 is a single or double carbon-carbon bond;
 is a single bond and is cis or trans when  is a double bond;
n and n' are each independently is 1 or 2;
m is zero or any positive integer; and
$R_1$, $R_2$, each $R_3$, and $R_4$ are independently hydrogen, an amino acid side chain, an alkyl group, or an aryl group.

51. The method of claim 50, wherein n' is 2 and m is 1.
52. The method of claim 50, wherein n' is 2 and m is 2.
53. The method of claim 50, wherein n' is 2 and n is 1.
54. The method of claim 50, wherein n' is 2 and n is 2.
55. The method of claim 44, wherein the peptide does not comprise the sequence FEGIYRLELLKAEEAN (SEQ ID NO: 9) or FEAIYRLELLKAEEAN (SEQ ID NO: 16).
56. The peptide of claim 15, wherein n' is 2 and m is 2.
57. The peptide of claim 15, wherein n' is 2 and n is 2.
58. The peptide of claim 18, wherein n' is 2 and m is 2.
59. The peptide of claim 18, wherein n' is 2 and n is 2.

* * * * *